US009861706B2

(12) United States Patent
Tolborg et al.

(10) Patent No.: US 9,861,706 B2
(45) Date of Patent: Jan. 9, 2018

(54) GLP-1 RECEPTOR AGONIST PEPTIDE GASTRIN CONJUGATES

(71) Applicant: Zealand Pharma A/S, Glostrup (DK)

(72) Inventors: Jakob Lind Tolborg, Herlev (DK); Trine Skovlund Ryge Neerup, Frederikssund (DK); Keld Fosgerau, Rødovre (DK); Torben Østerlund, Lund (SE); Dorthe Lennert Christensen Almholt, Greve (DK); Lone Frost Larsen, Charlottenlund (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 14/864,540

(22) Filed: Sep. 24, 2015

(65) Prior Publication Data

US 2016/0082118 A1    Mar. 24, 2016

Related U.S. Application Data

(63) Continuation of application No. 14/355,906, filed as application No. PCT/EP2012/071766 on Nov. 2, 2012, now Pat. No. 9,259,477.

(60) Provisional application No. 61/555,435, filed on Nov. 3, 2011.

(51) Int. Cl.
| | | |
|---|---|---|
| *A61K 38/00* | (2006.01) | |
| *A61K 47/48* | (2006.01) | |
| *A61K 45/06* | (2006.01) | |
| *A61K 38/22* | (2006.01) | |
| *A61K 38/26* | (2006.01) | |

(52) U.S. Cl.
CPC .... *A61K 47/48238* (2013.01); *A61K 38/2207* (2013.01); *A61K 38/26* (2013.01); *A61K 45/06* (2013.01); *A61K 47/481* (2013.01); *A61K 47/48038* (2013.01); *A61K 47/48046* (2013.01); *A61K 47/48107* (2013.01); *A61K 47/48215* (2013.01); *A61K 47/48246* (2013.01)

(58) Field of Classification Search
None
See application file for complete search history.

(56) References Cited

U.S. PATENT DOCUMENTS

| | | |
|---|---|---|
| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,795,861 A | 8/1998 | Kolterman et al. |
| 5,846,747 A | 12/1998 | Thorens et al. |
| 5,846,937 A | 12/1998 | Drucker |
| 6,006,753 A | 12/1999 | Efendic |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Hoist et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |
| 6,458,924 B2 | 10/2002 | Knudsen et al. |
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,056,734 B1 | 6/2006 | Egan et al. |
| 7,115,569 B2 | 10/2006 | Beeley et al. |
| 7,138,375 B2 | 11/2006 | Beeley et al. |
| 7,153,825 B2 | 12/2006 | Young et al. |
| 7,157,555 B1 | 1/2007 | Beeley et al. |

(Continued)

FOREIGN PATENT DOCUMENTS

| | | |
|---|---|---|
| EP | 1076066 A1 | 2/2001 |
| EP | 1196444 B1 | 6/2003 |
| EP | 1329458 A2 | 7/2003 |
| EP | 1421950 A1 | 5/2004 |
| EP | 2028192 A1 | 2/2009 |

(Continued)

OTHER PUBLICATIONS

US 9,555,078, 01/2017, Neerup et al. (withdrawn)
U.S. Appl. No. 14/116,268, Just et al.
U.S. Appl. No. 14/516,216, Riber et al.
U.S. Appl. No. 14/517,497, Riber et al.
U.S. Appl. No. 61/784,294, Tolborg et al.

(Continued)

*Primary Examiner* — Thomas S Heard
(74) *Attorney, Agent, or Firm* — Kristina Bieker-Brady; Clark & Elbing LLP

(57) ABSTRACT

The present invention relates, inter alia, to certain peptide conjugates, and to the use of the conjugates in the treatment of a variety of diseases or disorders, including diabetes (type 1 and/or type 2) and diabetes-related diseases or disorders.

19 Claims, 4 Drawing Sheets

(56) References Cited

U.S. PATENT DOCUMENTS

| | | | |
|---|---|---|---|
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,803,766 B2 | 9/2010 | Cruz |
| 7,858,740 B2 | 12/2010 | Beeley et al. |
| 7,928,065 B2 | 4/2011 | Young et al. |
| 7,935,786 B2 | 5/2011 | Larsen |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,727 B2 | 2/2014 | Larsen et al. |
| RE45,313 E | 12/2014 | Larsen et al. |
| 9,089,538 B2 | 7/2015 | Neerup et al. |
| 9,259,477 B2 | 2/2016 | Tolborg et al. |
| 2002/0137666 A1 | 9/2002 | Beeley et al. |
| 2004/0106547 A1 | 6/2004 | Larsen et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2009/0088369 A1 | 4/2009 | Steiness |
| 2011/0144008 A1 | 6/2011 | Larsen et al. |
| 2011/0245165 A1 | 10/2011 | Larsen et al. |
| 2011/0312878 A1 | 12/2011 | Larsen |
| 2013/0143793 A1 | 6/2013 | Neerup et al. |
| 2013/0210722 A1 | 8/2013 | Larsen et al. |
| 2014/0080757 A1 | 3/2014 | Tolborg et al. |
| 2014/0187483 A1 | 7/2014 | Steiness |
| 2014/0336107 A1 | 11/2014 | Tolborg et al. |
| 2014/0336356 A1 | 11/2014 | Larsen et al. |
| 2015/0111817 A1 | 4/2015 | Riber et al. |
| 2015/0111826 A1 | 4/2015 | Riber et al. |
| 2016/0184400 A1 | 6/2016 | Neerup et al. |
| 2017/0107267 A1 | 4/2017 | Larsen et al. |

FOREIGN PATENT DOCUMENTS

| | | | |
|---|---|---|---|
| EP | 1525219 B1 | 5/2009 |
| EP | 2112161 A2 | 10/2009 |
| JP | H07504670 A | 5/1995 |
| JP | 2001011095 A | 1/2001 |
| JP | 2007-525495 A | 9/2007 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | WO-98/08531 A1 | 3/1998 |
| WO | WO-98/8871 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |
| WO | WO-99/43708 A1 | 9/1999 |
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |
| WO | WO-02/34285 A2 | 5/2002 |
| WO | WO-03/022304 A1 | 3/2003 |
| WO | WO-2004/005342 A1 | 1/2004 |
| WO | WO-2005/072045 A2 | 8/2005 |
| WO | WO-2005/077072 A2 | 8/2005 |
| WO | WO-2007/095737 A1 | 8/2007 |
| WO | WO-2007/100535 A2 | 9/2007 |
| WO | WO-2008/071010 A1 | 6/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/077737 A2 | 6/2009 |
| WO | WO-2009/155257 A1 | 12/2009 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/096052 A1 | 8/2010 |
| WO | WO-2011/084808 A2 | 7/2011 |
| WO | WO-2011/088837 A1 | 7/2011 |
| WO | WO-2011/134471 A1 | 11/2011 |

OTHER PUBLICATIONS

"European public assessment report (EPAR): EPAR summary for the public" EMEA. (11 pages) (2006).

Action Closing Prosecution in Inter Partes Reexam 95/000,276, mailed Mar. 17, 2011 (25 pages).

Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).

Bailey et al., "Glucagon-like peptide-1 and the entero-insular axis in obese hyperglycaemic (ob/ob) mice," Life Sci. 40(6):521-525 (1987).

Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008) (13 pages).

Bedford et al., "Amino acid structure and 'difficult sequences' in solid phase peptide synthesis," Int J Peptide Protein Res. 40(3-4):300-7 (1992).

Behme et al., "Glucagon-like peptide 1 improved glycemic control in type 1 diabetes," BMC Endocr Disord. 3(1):3 (2003) (9 pages).

Burcelin et al., "Long-lasting antidiabetic effect of a dipeptidyl peptidase IV-resistant analog of glucagon-like peptide-1," Metabolism. 48(2):252-258 (1999).

Buse et al., "The effect of epinephrine, glucagon, and the nutritional state on the oxidation of branched chain amino acids and pyruvate by isolated hearts and diaphragms of the rat," J Biol Chem. 248(2):697-706 (1973).

(56) References Cited

OTHER PUBLICATIONS

Buse, "Progressive use of medical therapies in type 2 diabetes," Diabetes Spectrum. 13(4):211-220 (2000).
Byrne et al., "Inhibitory effects of hyperglycaemia on fed jejunal motility: potential role of hyperinsulinaemia," Eur J Clin Invest. 28(1):72-78 (1998).
Carpenter et al., "Rational design of stable lyophilized protein formulations: some practical advice," Pharm Res. 14(8):969-75 (1997).
Chen et al., "Evidence that the Diabetes gene encodes the leptin receptor: identification of a mutation in the leptin receptor gene in db/db mice," Cell. 84(3):491-5 (1996).
Chen et al., "Tissue-specific expression of unique mRNAs that encode proglucagon-derived peptides or exendin 4 in the lizard," J Biol Chem. 272(7):4108-15 (1997).
Cleland et al., "The development of stable protein formulations: a close look at protein aggregation, deamidation, and oxidation," Crit Rev Ther Drug Carrier Syst. 10(4):307-77 (1993).
Cohen et al., "Oxyntomodulin suppresses appetite and reduces food intake in humans," J Clin Endocrinol Metab. 88(10):4696-4701 (2003).
Coleman, "Effects of parabiosis of obese with diabetes and normal mice," Diabetologia. 9(4):294-8 (1973).
D'Alessio et al., "Glucagon-like peptide 1 enhances glucose tolerance both by stimulation of insulin release and by increasing insulin-independent glucose disposal," J Clin Invest. 93(5):2263-66 (1994).
Dakin et al., "Peripheral oxyntomodulin reduces food intake and body weight gain in rats," Endocrinology. 145(6):2687-2695 (2004).
De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like-peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, filed Nov. 25, 2013 (29 pages).
Delgado et al., "The uses and properties of PEG-linked proteins," Crit Rev Ther Drug Carrier Syst. 9(3,4):249-304 (1992).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Drucker, "Glucagon-like peptides," Diabetes. 47(2):159-69 (1998).
Edvell et al., "Initiation of increased pancreatic islet growth in young normoglycemic mice (Umea +/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions (11 pages) (2006).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
European Medicines Agency, European Public Assessment Report (EPAR) for European Application 03762471.5, updated in Jan. 2006 (11 pages).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
European Search Report for European Patent Application No. 99610043, dated Jan. 18, 2000 (2 pages).
Extended European Search Report for European Patent Application No. 08016668, dated Jan. 14, 2009 (4 pages).
Extended European Search Report for European Patent Application No. 11774431.8, dated Sep. 30, 2013 (11 pages).
Farah et al., "Studies on the pharmacology of glucagon," J Pharmacol Exp Ther. 129:49-55 (1960).
Fineman et al., "AC2993 (Synthetic Exendin-4) Improved Glycemic Control in Patients With Type 2 Diabetes During 28 Days of Treatment in a Multicenter, Randomized, Triple-Blind, Placebo-Controlled Study," Diabetes 51 (Supplement 2):A85, Abstract 343-0R, Abstract Book 62"d Scientific Sessions. POSTER. Jun. 14-18, 2002.
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51(Supplement 2):A85, Abstract Book, 62nd Scientific Sessions (2002) (3 pages).
Fosgerau et al., "The novel GLP-1-gastrin dual agonist, ZP3022, increases beta-cell mass and prevents diabetes in db/db mice," Diabetes Obes Metab. 15(1):62-71 (2013).
Francis et al., "PEGylation of cytokines and other therapeutic proteins and peptides: the importance of biological optimisation of coupling techniques," Int J Hematol. 68(1):1-18 (1998).
Gombotz et al. "Biodegradable polymers for protein and peptide drug delivery," Bioconjug Chem. 6(4):332-351 (1995).
Greig et al., "Once daily injection of exendin-4 to diabetic mice achieves long-term beneficial effects on blood glucose concentrations," Diabetologia. 42(1):45-50 (1999).
Grieve et al., "Emerging cardiovascular actions of the incretin hormone glucagon-like peptide-1: Potential therapeutic benefits beyond glycaemic control?," Br J Pharmacol. 157(8):1340-51 (2009).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-90 (1995).
Göke et al., "Distribution of GLP-1 binding sites in the rat brain: Evidence that exendin-4 is a ligand of brain GLP-1 binding sites," Eur J Neurosci. 7(11):2294-2300 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-55 (1993).
Haffner et al., "Intensive lifestyle intervention or metformin on inflammation and coagulation in participants with impaired glucose tolerance," Diabetes. 54(4):1566-72 (2005).
Hamad et al., "Pharmacologic therapy of chronic heart failure," Am J Cardiovasc Drugs. 7(4):235-48 (2007).
Harikae, "The effects of a behavioral program in the obese NIDDM patients-observations on daily activity, degree of obesity and blood sugar control," Bulletin of the School of Nursing, Yamaguchi Prefectural University 2:1-13/E (1998) (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-81 (1984).
Holst, "Enteroglucagon," Annu Rev Physiol. 59:257-71 (1997).
Holst, "Glucagon-like peptide-1, a gastrointestinal hormone with a pharmaceutical potential," Curr Med Chem. 6(11):1005-17 (1999).
Holst, "The physiology of glucagon-like peptide 1," Physiol Rev. 87(4): 1409-39 (2007).
Hudecz et al., "Synthesis, conformation, biodistribution, and in vitro cytotoxicity of daunomycin-branched polypeptide conjugates," Bioconjug Chem. 3(1):49-57 (1992).
Hui et al., "The short half-life of glucagon-like peptide-1 in plasma does not reflect its long-lasting beneficial effects," Eur J Endocrinol. 146(6):863-9 (2002).

(56) References Cited

OTHER PUBLICATIONS

Igaki et al., "Investigation of effectiveness of low intensity exercise on body fat reduction in diabetics," J.Japan Phys Ther Assoc, 26:270-4 (1999).
Ingwall et al., "Is the failing heart energy starved? On using chemical energy to support cardiac function," Circ Res. 95(2):135-45 (2004).
International Preliminary Examination Report for International Application No. PCT/DK03/00463, dated Sep. 20, 2004 (5 pages).
International Preliminary Report on Patentability for International Patent Application No. PCT/DK2003/00463, completed Sep. 20, 2004 (5 pages).
International Search Report and Written Opinion for International Application No. PCT/IB2012/001090, dated Jan. 25, 2013 (15 pages).
International Search Report and Written Opinion for International Patent Application No. PCT/EP2012/071766, dated Feb. 15, 2013 (10 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2011/050133 dated Oct. 6, 2011 (5 pages).
International Search Report for International Patent Application No. PCT/DK2003/00463, dated Oct. 22, 2003 (7 pages).
International Search Report for International Patent Application No. PCT/DK2011/050018, dated May 30, 2011 (6 pages).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation.," Circulation. 119(14):1977-2016 (2009).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Klyose et al., "Glucose tolerance screening method using a combination of fasting plasma glucose and hemoglobin A1c," J. Japan Diab Soc, 30:325:331 (1987).
Korc, "Islet growth factors: curing diabetes and preventing chronic pancreatitis?," J Clin Invest. 92(3):1113-4 (1993).
Krchnák et al., "Aggregation of resin-bound peptides during solid-phase peptide synthesis. Prediction of difficult sequences," Int J Pept Protein Res. 42(5):450-4 (1993).
Larsen et al., "Sequence-assisted peptide synthesis (SAPS)," J Pept Res. 52(6):470-6 (1998).
Leiter et al., "Influence of dietary carbohydrate on the induction of diabetes in C57BL/KsJ-db/db diabetes mice," J Nutr. 113(1):184-95 (1983).
Levey et al., "Activation of adenyl cyclase by glucagon in cat and human heart," Circ Res. 24(2):151-6 (1969).
Lopaschuk et al., "Measurements of fatty acid and carbohydrate metabolism in the isolated working rat heart," Mol Cell Biochem. 172(1-2):137-47 (1997).
Loyter et al., "Mechanisms of DNA uptake by mammalian cells: fate of exogenously added DNA monitored by the use of fluorescent dyes," Proc Natl Acad Sci USA. 79(2):422-6 (1982).
López-Delgado et al., "Effects of glucagon-like peptide 1 on the kinetics of glycogen synthase a in hepatocytes from normal and diabetic rats," Endocrinology. 139(6):2811-17 (1998).
Manning et al., "Stability of protein pharmaceuticals," Pharm Res. 6(11):903-18 (1989).
Matthes et al., "Simultaneous rapid chemical synthesis of over one hundred oligonucleotides on a microscale," EMBO J. 3(4):801-5 (1984).
Mayer et al., "Effect of glucagon on cyclic 3',5'-AMP, phosphorylase activity and contractility of heart muscle of the rat," Circ Res. 26(2):225-33 (1970).

Meurer et al., "Properties of native and in vitro glycosylated forms of the glucagon-like peptide-1 receptor antagonist exendin (9-39)," Metabolism. 48(6):716-24 (1999).
Meyer et al., Effects of conformation on the Chemical Stability of Pharmaceutically Relevant Polypeptides. *Rational design of stable protein formulations*. Carpenter and Manning, 85-6 (2002).
Mojsov, "Structural requirements for biological activity of glucagon-like peptide-I," Int J Pept Protein Res. 40(3-4):333-43 (1992).
Nauck et al., "Glucagon-like peptide 1 and its potential in the treatment of non-insulin-dependent diabetes mellitus," Horm Metab Res. 29(9):411-6 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).
Neubauer et al., "Myocardial phosphocreatine-to-ATP ratio is a predictor of mortality in patients with dilated cardiomyopathy," Circulation. 96(7):2190-6 (1997) (9 pages).
Neumann et al., "Gene transfer into mouse lyoma cells by electroporation in high electric fields," EMBO J. 1(7):841-5 (1982).
Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-8 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-61 (2004).
Notice of Opposition and Opposition from European Patent Application No. 1525219, filed Feb. 25, 2010.
Notice of Opposition for European Patent No. 1525219, dated Feb. 26, 2010 (24 pages).
Opposition from European Patent No. 1525219, dated Feb. 25, 2010.
Orskov, "Glucagon-like peptide-1, a new hormone of the entero-insular axis," Diabetologia. 35(8):701-11 (1992).
Owens et al., "Insulins today and beyond," Lancet. 358(9283):739-46 (2001).
Parkes et al., "Insulinotropic actions of exendin-4 and glucagon-like peptide-1 in vivo and in vitro," Metabolism. 50(5):583-9 (2001).
Partial European Search Report for European Patent Application No. 03005786, dated Oct. 23, 2003 (6 pages).
Partial European Search Report for European Patent Application No. 99610043, dated Jan. 18, 2000 (4 pages).
Pederson et al., "Improved glucose tolerance in Zucker Fatty Rats by oral administration of the dipeptidyl peptidase IV inhibitor isoleucine thiazolidide," Diabetes. 47(8):1253-8 (1998).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447 (2002) (2 pages).
Pocai et al., "Glucagon-like peptide 1/glucagon receptor dual agonism reverses obesity in mice," Diabetes. 58(10):2258-66 (2009).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).
Poon et al., "Exenatide improves glycemic control and reduces body weight in subjects with type 2 diabetes: a dose-ranging study," Diabetes Technol Ther. 7(3):467-77 (2005).
Pratesi et al., "Poly-L-aspartic acid as a carrier for doxorubicin: a comparative in vivo study of free and polymer-bound drug," Br J Cancer. 52(6):841-848 (1985).
Pridal et al., "Absorption of glucagon-like peptide-1 can be protracted by zinc or protamine," Int J Pharm 136:53-59 (1996).

(56) References Cited

OTHER PUBLICATIONS

Raufman et al, "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).
Raufman et al. "Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).
Raufman, "Bioactive peptides from lizard venoms," Regul Pept. 61(1):1-18 (1996).
Ritzel et al., "A synthetic glucagon-like peptide-1 analog with improved plasma stability," J Endocrinol. 159(1):93-102 (1998).
Roach et al., "Improved postprandial glycemic control during treatment with humalog Mix25, a novel protamine-based insulin lispro formulation. Humalog Mix25 Study Group," Diabetes Care. 22(8):1258-61 (1999).
Robberecht et al., "Comparative efficacy of seven synthetic glucagon analogs, modified in position 1, 2, and/or 12, on liver and heart adenylate cyclase from rat," Peptides. 7(Suppl 1):109-12 (1986).
Rolin et al., "The long-acting GLP-1 derivative NN2211 ameliorates glycemia and increases beta-cell mass in diabetic mice," Am J Physiol Endocrinol Metab. 283(4):E745-52 (2002).
Rooman et al., "Gastrin stimulates beta-cell neogenesis and increases islet mass from transdifferentiated but not from normal exocrine pancreas tissue," Diabetes. 51(3):686-90 (2002).
Saraceni et al., "Effects of glucagon-like peptide-1 and long-acting analogues on cardiovascular and metabolic function," Drugs R D. 8(3):145-53 (2007).
Sowden et al., "Oxyntomodulin increases intrinsic heart rate in mice independent of the glucagon-like peptide-1 receptor," Am J Physiol Regul Integr Comp Physiol. 292(2): R962-70 (2007).
Sporn et al., "Chemoprevention of cancer," Carcinogenesis. 21(3):525-530 (2000).
Stoffers et al., "Insulinotropic glucagon-like peptide 1 agonists stimulate expression of homeodomain protein IDX-1 and increase islet size in mouse pancreas," Diabetes. 49(5):741-8 (2000).
Suarez-Pinzon et al., "Combination therapy with epidermal growth factor and gastrin increases beta-cell mass and reverses hyperglycemia in diabetic NOD mice," Diabetes. 54(9):2596-601 (2005).
Suarez-Pinzon et al., "Combination therapy with glucagon-like peptide-1 and gastrin restores normoglycemia in diabetic NOD mice," Diabetes. 57(12):3281-8 (2008).
Tang-Christensen et al., "Central administration of GLP-1-(7-36) amide inhibits food and water intake in rats," Am J. Physiol. 271(4 Pt 2):R848-56 (1996).
Thorkildsen et al., "The exendin analogue ZP10 increases insulin mRNA expression in db/db mice," Nedergaard Symposium, Odense, Denmark, Jan. 24, 2002 (Poster presentation).
Thorkildsen et al., "ZP10—A New GLP-1 agonist that increases insulin mRNA expression," Nedergaard Symposium, Odense, Denmark, Jan. 24, 2002 (abstract only) (1 page).
Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation.
Tomita et al., "Pancreatic islets of obese hyperglycemic mice (ob/ob)," Pancreas. 7(3):367-75 (1992).
Tourrel et al., "Persistent improvement of type 2 diabetes in the Goto-Kakizaki rat model by expansion of the beta-cell mass during the prediabetic period with glucagon-like peptide-1 or exendin-4," Diabetes. 51(5):1443-52 (2002).
Transition Therapeutics Inc., "Lilly and Transition Therapeutics announce licensing and collaboration agreement. Lilly to acquire exclusive rights to gastrin based therapies program for diabetes," <http://www.transitiontherapeutics.com/media/news.php>, retrieved May 28, 2015 (2 pages).
Transition Therapeutics Inc., "Positive preclinical data with Novo Nordisk A/S long-acting GLP-1 analog and gastrin combination presented at American Diabetes Association Meeting," <http://www.transitiontherapeutics.com/media/news.php>, retrieved on May 28, 2015 (1 page).
Translation of Office Action for Japanese Patent Application No. 2004-518465, dated Nov. 24, 2009 (6 pages).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Turton et al., "A role for glucagon-like peptide-1 in the central regulation of feeding," Nature 379(6560):69-72 (1996).
U.S. Appl. No. 14/095,667, filed Dec. 3, 2013 (99 pages).
U.S. Appl. No. 14/116,268, filed Nov. 7, 2013 (164 pages).
Uesaka et al., "Glucagon-like peptide isolated from the eel intestine: Effects on atrial beating," J Exp Bio. 204(Pt 17):3019-26 (2001).
Underwood et al., "Crystal structure of glucagon-like peptide-1 in complex with the extracellular domain of the glucagon-like peptide-1 receptor," J Biol Chem. 285(1):723-30 (2010).
Uttenthal et al., "Molecular forms of glucagon-like peptide-1 in human pancreas and glucagonomas," J Clin Endocrinol Metabol. 61(3):472-479 (1985).
Villa-Komaroff et al., "A bacterial clone synthesizing proinsulin," Proc Natl Acad Sci USA. 75(8):3727-31 (1978).
Wang et al., "Glucagon-like peptide-1 treatment delays the onset of diabetes in 8 week-old db/db mice," Diabetologia. 45(9):1263-73 (2002).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21):7287-7302 (1983).
Written Opinion for Singapore Patent Application No. 2012078382, dated Mar. 13, 2015 (14 pages).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes. 48(5):1026-34 (1999).
Young et al., "Physiological and genetic factors affecting transformation of Bacillus subtilis," J Bacteriol. 81:823-9 (1961).
Zalipsky, "Functionalized poly(ethylene glycol) for preparation of biologically relevant conjugates," Bioconjug Chem. 6(2):150-165 (1995).
Zander et al., "Additive glucose-lowering effects of glucagon-like peptide-1 and metformin in type 2 diabetes," Diabetes Care. 24(4):720-5 (2001).
Zhao et al., "Direct effects of glucagon-like peptide-1 on myocardial contractility and glucose uptake in normal and postischemic isolated rat hearts," J Pharmacol Exp Ther. 317(3):1106-13 (2006).
Zhou et al., "Glucagon-like peptide 1 and exendin-4 convert pancreatic AR42J cells into glucagon- and insulin-producing cells," Diabetes. 48(12): 2358-66 (1999).
Christensen et al., "Lixisenatide, a novel GLP-1 receptor agonist for the treatment of type 2 diabetes mellitus," IDrugs 12(8):503-13 (2009).
Curriculum Vitae (CV) of Keld Fosgerau, Ph.D. (9 pages).
Experimental Report provided in response to opposition filed against European Patent No. 1525219, filed Oct. 5, 2011 (4 pages).
Grounds of Appeal by F. Hoffmann-La Roche AG for European Patent No. 1525219, filed Aug. 10, 2012 (35 pages).
Grounds of Appeal by Novo Nordisk A/S for European Patent No. 1525219, filed Aug. 3, 2012 (27 pages).
ICH Harmonised Tripartite Guideline, Feb. 5, 1998 (39 pages).

(56) References Cited

OTHER PUBLICATIONS

International Dictionary of Medicine and Biology in Three Volumes: vol. II. *John Wiley & Sons*, New York,1328 (1986) (3 pages).
Kitamura, "Is the "drug holiday" harmful?," Keio J Med. 25(3):131-7 (1976).
Larsen et al., "Glucagon-like peptide-1 infusion must be maintained for 24 h/day to obtain acceptable glycemia in type 2 diabetic patients who are poorly controlled on sulphonylurea treatment," Diabetes Care. 24(8):1416-21 (2001).
Meier et al., "Absence of a memory effect for the insulinotropic action of glucagon-like peptide 1 (GLP-1) in healthy volunteers," Horm Metab Res. 35(9):551-6 (2003).
Notarized Affidavit from the British Library regarding European Journal of Endocrinology, vol. 146, No. 6, Jun. 2002, dated Apr. 21, 2011 (5 pages).
Notice of Appeal of Opposition Decision for European Patent No. 1525219 by F. Hoffmann-La Roche AG, filed May 21, 2012 (1 page).
Notice of Appeal of Opposition Decision for European Patent No. 1525219 by Novo Nordisk A/S, filed Apr. 23, 2012 (1 page).
O'Shaughnessy et al., "Alpha-difluoromethylornithine as treatment for metastatic breast cancer patients," Clin Cancer Res. 5(11):3438-44 (8 pages) (1999).
PDR Medical Dictionary. Medical Economics, Montvale, New Jersey, p. 522 (1995) (3 pages).
Prescribing information for Victoza (31 pages).
Suarez-Pinzon et al., "Combination therapy with glucagon-like peptide-1 and gastrin induces beta-cell neogenesis from pancreatic duct cells in human islets transplanted in immunodeficient diabetic mice," Cell Transplant. 17(6):631-40 (2008).
Table of Claims anticipated by WO 00/09666 (9 pages).
Tourrel et al., "Glucagon-like peptide-1 and exendin-4 stimulate beta-cell neogenesis in streptozotocin-treated newborn rats resulting in persistently improved glucose homeostasis at adult age," Diabetes 50(7):1562-70 (2001).
Wodarz et al., "Specific therapy regimes could lead to long-term immunological control of HIV," Proc Natl Acad Sci U.S.A. 96(25):14464-9 (1999).

Figure 7
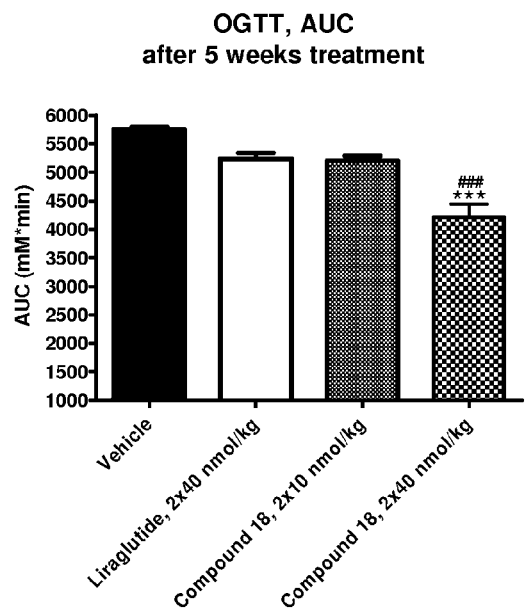
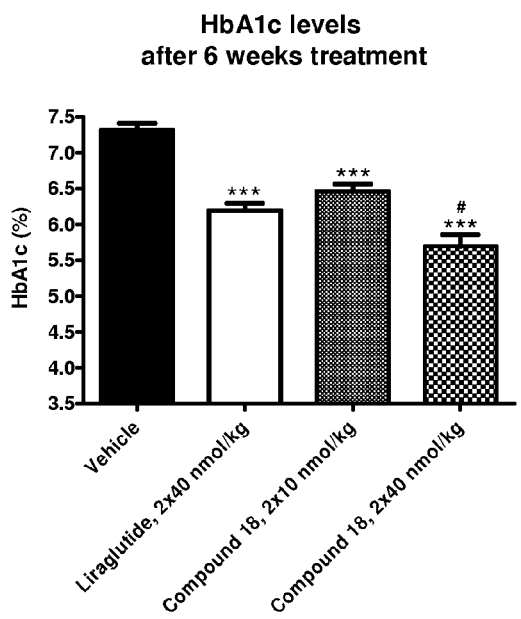
Figure 8

GLP-1 RECEPTOR AGONIST PEPTIDE GASTRIN CONJUGATES

FIELD OF THE INVENTION

The present invention relates, inter alia, to certain peptide conjugates, and to the use of the conjugates in the treatment and/or prevention of a variety of diseases or disorders, including diabetes (type 1 and/or type 2) and diabetes-related diseases or disorders.

BACKGROUND OF THE INVENTION

Diabetes, notably type 1 and type 2 diabetes, together with obesity, which is believed to be a major causal factor in the development of type 2 diabetes, constitute a major and even growing worldwide health problem. Diseases or disorders that may develop as a consequence of diabetes include cardiovascular and peripheral vascular disease, micro- and macrovascular complications, stroke and possibly certain forms of cancer.

Diabetes is characterized by a defective physiological regulation of blood glucose levels. Among the underlying conditions that may lead to diabetes are reductions in or the loss of pancreatic β-cell mass and function, with attendant reduction in or loss of endogenous Insulin production, and/or Insulin resistance (reduced sensitivity to insulin), i.e. reduction in or loss of the ability of endogenous insulin to bring about adequate regulation of blood glucose levels.

A number of hormones that lower blood glucose levels are secreted by the gastrointestinal mucosa in response to the presence and absorption of nutrients in the gut. These include glucagon-like peptide-1 (GLP-1), glucose-dependent insulinotropic peptide (GIP), gastrin, and secretin.

GLP-1 [see, e.g., Ørskov, *Diabetologia* 35: 701-711 (1992)] is produced by tissue processing of proglucagon, a 180 amino acid peptide [see, e.g., Drucker, *Diabetes* 47: 159-169 (1998)]. The overall sequence of proglucagon contains the 29 amino acid sequence of glucagon, the 36 or 37 amino acid sequence of GLP-1, and the 34 amino acid sequence of glucagon-like peptide-2 (GLP-2; an intestinotrophic peptide).

The so-called exendins, which constitute another group of peptides that lower blood glucose levels, have some sequence similarity (53%) to GLP-1(7-36) [see, e.g., Goke et al., *J. Biol. Chem.* 268: 19650-19655 (1993)]. The exendins are found in the saliva of Helodermatidae species (beaded lizards). Exendin-3 is present in the saliva of *Heloderma horridum* (Mexican beaded lizard), while exendin-4 is present in the saliva of *Heloderma suspectum* (Gila monster). The amino acid sequence of exendin-4, which differs from that of exendin-3 at positions two and three, is

HGEGTFTSDLSKQMEEEAVRLFIEWLKNGGPSS-
GAPPPS-NH$_2$ (SEQ ID NO: 44)

Exendin-4 has been reported to be a potent GLP-1 receptor agonist on isolated rat insulinoma cells [Goke et al., loc. cit.]. WO 99/07404 discloses that exendin-4 administered systemically lowers blood glucose levels by 40% in diabetic db/db mice, and a long-lasting blood glucose lowering effect of once-daily intraperitoneal injection of exendin-4 in diabetic ob/ob mice has also been reported [Grieg et al., *Diabetologia* 42: 45-50 (1999)].

U.S. Pat. No. 5,424,286 and WO 98/05351 disclose that exendin-3, exendin-4 and exendin agonists may be used for the treatment of diabetes, for reducing gastric motility and delaying gastric emptying, and for prevention of hyperglycemia, and WO 98/30231 further discloses that they may be used for reducing food intake.

The peptide hormone gastrin is secreted from cells in the gastric mucosa and from G cells in the duodenum, and among the major physiological roles of the hormone in humans are stimulation of secretion of gastric acid (i.e. HCl) and aiding in gastric motility. There are indications that gastrin may play a role in islet neogenesis, i.e. stimulation of insulin-secreting β-cell growth in the pancreatic islets [see, e.g., Korc, M., *J. Clin. Invest.*, 92: 1113-1114 (1993); Rooman et al. *Diabetes* 51: 686-690 (2002)], and thereby contribute to regulation of blood glucose.

Gastrin shares receptors with another gastrointestinal peptide hormone, cholecystokinin (CCK). The receptors CCK-A R and CCK-B R have different affinities for gastrin and CCK variants. CCK-A R (or CCK R1) acts primarily as a receptor for sulfated CCK, whereas CCK-B R (or CCK R2) binds both CCK and gastrin equally well. CCK-B R is considered to be the "gastrin receptor" due to the higher levels of gastrin compared to CCK in plasma [Foucaud et al. *Reg. Peptides* 145: 17-23 (2008)].

CCK-B R can initiate several intracellular pathways upon binding of ligand, which is considered to be the reason for the diverse physiological roles of CCK. A key pathway downstream of CCK-B R is the MAPK (mitogen activated protein kinases) or ERK (extra-cellular regulated kinases) pathway, which is also activated by several growth hormones. Since CCK-B R is expressed in the pancreas, gastrin is able to contribute to cell proliferation and islet regeneration in this tissue.

In humans, gastrin occurs primarily in three forms, viz. gastrin34, gastrin17 and gastrin14 (with reference to the total number of amino acids in the sequence in question). Gastrin6 has also been identified. The shorter forms are generated by cleavage of C-terminally amidated gastrin34; thus gastrin17 consists of the last 17 C-terminal residues of gastrin34 (corresponding to progastrin (55-71), gastrin14 consists of the last 14 C-terminal residues of gastrin34 (corresponding to progastrin (58-71), and gastrin6 consists of only the last 6 C-terminal residues of gastrin34 (corresponding to progastrin (66-71). In human gastrin17 the N-terminal amino acid residue is a pyroglutamic acid (Pyro-Glu) residue. The amidated C-terminal 6 amino acids are the key receptor-binding residues of gastrin.

SUMMARY OF THE INVENTION

It has now been found that certain conjugates comprising two covalently coupled or linked peptide moieties may exhibit unexpectedly high therapeutic activity in the treatment, for example, of diabetes (type 1 and/or type 2 diabetes), or of various other diabetes-related diseases or disorders, by comparison with the therapeutic activity of a combination of the two individual peptides in question.

In a broad aspect, the invention provides a peptide conjugate of a GLP-1 receptor agonist and gastrin, in particular gastrin with a substitution at position 15 in gastrin17 (corresponding to position 4 in gastrin6) selected from Leu, Nle, Phe and Thr. More particularly, the invention provides peptide conjugates of exendin-4 and gastrin.

In some embodiments, the invention thus provides a peptide conjugate having the formula I $$R^1\text{-}Z_a\text{-}L_a\text{-}Y_a\text{-}R^2 \qquad \text{(I) (SEQ ID NO: 45)}$$

wherein
$R^1$ is H, $C_{1-4}$ alkyl, acetyl, formyl, benzoyl or trifluoroacetyl;
$R^2$ is OH or NH$_2$; and $Z_a$ is a peptide sequence having the formula Ia His-Gly-Glu-Gly-Thr-Phe-Thr-Ser-Z9-Leu-Ser-Z12-
Z13-Z14-Glu-Z16-Glu-Ala-Val-Z20-Leu-Phe-
Ile-Z24-Z25-Leu-Z27-Z28    (Ia) (SEQ ID NO.: 46)

wherein
Z9 is selected from Asp and Glu;
Z12 is selected from Lys, Arg and Orn;
Z13 is selected from Gln and Tyr;
Z14 is selected from Met and Leu;
Z16 is selected from Glu, Cys, Arg, Orn and Lys;
Z20 is selected from Arg, Lys and Orn;
Z24 is selected from Lys, Arg, Orn and Glu;
Z25 is selected from Trp, Lys, Cys and Phe;
Z27 is selected from Lys, Arg and Orn; and
Z28 is selected from Asn and Asp or is absent;
La is a peptide sequence having the formula Ib L1-L2-L3-L4    (Ib) (SEQ ID NO: 61)

wherein
L1 is selected from Orn, 8Ado, Cys, Lys and Gln or is absent;
L2 is selected from Orn, 8Ado, Cys, Lys and Gln or is absent;
L3 is selected from Orn, 8Ado, Cys, Lys and Gln or is absent; and
L4 is selected from Orn, 8Ado, Cys, Lys and Gln or is absent; and
$Y_a$ is a peptide sequence having the formula Ic Y12-Y13-Y14-Y15-Asp-Y17    (Ic) (SEQ ID NO: 62)

wherein
Y12 is selected from Tyr and Ala or is absent;
Y13 is selected from Gly and Ala or is absent;
Y14 is selected from Trp, 1Nal and Phe;
Y15 is selected from Met, Leu, Nle, Thr and Phe; and
Y17 is selected from Phe and 3-(3-pyridyl)-alanine;
wherein at least one of Lys, Orn or Cys in formula Ia and Ib is further conjugated to a lipophilic and/or a biotinylic substituent and/or pegylated;
or a pharmaceutically acceptable salt or solvate thereof.

In further embodiments, the invention provides a peptide conjugate of formula I wherein
$Z_a$ is a peptide sequence having the formula IIa His-Gly-Glu-Gly-Thr-Phe-Thr-Ser-Z9-Leu-Ser-Lys-
Z13-Z14-Glu-Z16-Glu-Ala-Val-Arg-Leu-Phe-
Ile-Glu-Z25-Leu-Lys-Z28    (IIa) (SEQ ID NO: 48)

wherein
Z9 is selected from Glu and Asp;
Z13 is selected from Gln and Tyr;
Z14 is selected from Met and Leu;
Z16 is selected from Glu, Cys and Lys;
Z25 is selected from Lys, Phe, Cys and Trp; and
Z28 is selected from Asn and Asp or is absent;
$L_a$ is a peptide sequence having the formula Ib as described above; and
$Y_a$ is a peptide sequence having the formula IIc Tyr-Gly-Trp-Y15-Asp-Phe    (IIc) (SEQ ID NO: 49)

wherein
Y15 is selected from Leu and Thr; and
wherein at least one of the Lys residues in position Z16 and Z25 of formula IIa is further conjugated to a lipophilic and/or a biotinylic substituent and/or pegylated;
or a pharmaceutically acceptable salt or solvate thereof.

In specific embodiments, the invention relates to a peptide conjugate having the formula:

H-HGEGTFTSDLSKQLEEEAVRLFIEWLKN-
8Ado-K(hexadecanoyl-isoGlu)-8Ado-YG-
WLDF-NH$_2$    (Compound 1) (SEQ ID NO: 1)

H-HGEGTFTSDLSKQLEEEAVRLFIE-K(hexade-
canoyl-isoGlu)-LKN-8Ado-8Ado-YGWLDF-
NH$_2$    (Compound 2) (SEQ ID NO: 2)

H-HGEGTFTSDLSKQLE-K(hexadecanoyl-isoGlu)-
EAVRLFIEWLKN-8Ado-
8Ado-YGWLDF-NH$_2$    (Compound 3) (SEQ ID NO: 3)

H-HGEGTFTSDLSKQMEEEAVRLFIEWLKN-
8Ado-C(Biotin-Mal)-8Ado-
YGWLDF-NH$_2$    (Compound 4) (SEQ ID NO: 4)

H-HGEGTFTSDLSKQLEEEAVRLFIE-C(Biotin-
Mal)-LKN-8Ado-8Ado-
YGWLDF-NH$_2$    (Compound 5) (SEQ ID NO: 5)

H-HGEGTFTSDLSKQLE-C(Biotin-Mal)-EAVR-
LFIEWLKN-8Ado-8Ado-
YGWLDF-NH$_2$    (Compound 6) (SEQ ID NO: 6)

H-HGEGTFTSELSKYLEEEAVRLFIE-K(hexade-
canoyl-isoGlu)-LK-8Ado-
8Ado-YGWLDF-NH$_2$    (Compound 7) (SEQ ID NO: 7)

H-HGEGTFTSELSKYLEEEAVRLFIE-K(hexade-
canoyl-isoGlu)-LK-8Ado-
QQYGWLDF-NH$_2$    (Compound 8) (SEQ ID NO: 8)

or a pharmaceutically acceptable salt or solvate thereof.

In other embodiments, the invention provides a peptide conjugate having the formula III $R^1$-$Z_b$-$L_b$-$Y_b$-$R^2$    (III) (SEQ ID NO: 50)

wherein
$R^1$ is H, $C_{1-4}$ alkyl, acetyl, formyl, benzoyl or trifluoroacetyl;
$R^2$ is OH or NH$_2$; and
$Z_b$ is a peptide sequence having the formula IIIa His-Gly-Glu-Gly-Thr-Phe-Thr-Ser-Glu-Leu-Ser-Lys-
Tyr-Leu-Glu-Glu-Glu-Ala-Val-Arg-Leu-Phe-Ile-
Glu-Z25-Leu-Lys-Z28    (IIIa) (SEQ ID NO: 51)

wherein
Z25 is selected from Phe and Trp; and
Z28 is selected from Asn and Asp or is absent;
$L_b$ is a peptide sequence having the formula IIIb L5-L6-L7-L8    (IIIb) (SEQ ID NO: 63)

wherein
L5 is selected from 8Ado, 8Aoc, Ala, Gly and Gln or is absent;
L6 is selected from 8Ado, 8Aoc, Ala, Gly and Gln or is absent;
L7 is selected from 8Ado, 8Aoc, Ala, Gly and Gln or is absent; and
L8 is selected from 8Ado, 8Aoc, Ala, Gly and Gln or is absent; and
$Y_b$ is a peptide sequence having the formula IIIc Y10-Y11-Tyr-Gly-Trp-Y15-Asp-Phe    (IIIc) (SEQ ID NO: 52)

wherein
Y10 is Glu or is absent;
Y11 is Ala or is absent; and
Y15 is selected from Leu and Thr;
or a pharmaceutically acceptable salt or solvate thereof;
provided that formula III is not H-HGEGTFTSELSKYLEEEAVRLFIEFLK-8Ado-
8Ado-YGWLDF-NH$_2$    (SEQ ID NO: 53);

H-HGEGTFTSELSKYLEEEAVRLFIEFLKYG-
WLDF-NH$_2$    (SEQ ID NO: 54); and

H-HGEGTFTSELSKYLEEEAVRLFIEFLK-8Ado-
YGWLDF-NH$_2$    (SEQ ID NO: 55).

In further embodiments, the invention provides a peptide conjugate of formula III wherein
$Z_b$ is a peptide sequence having the formula IVa His-Gly-Glu-Gly-Thr-Phe-Thr-Ser-Glu-Leu-Ser-Lys-
  Tyr-Leu-Glu-Glu-Glu-Ala-Val-Arg-Leu-Phe-Ile-
  Glu-Z25-Leu-Lys-Asn  (IVa) (SEQ ID NO: 57)

wherein
Z25 is selected from Lys, Phe and Trp; and
$L_b$ is a peptide sequence having the formula IIIb as described above
$Y_b$ is a peptide sequence having the formula IVc Tyr-Gly-Trp-Y15-Asp-Phe  (IVc) (SEQ ID NO: 58)

wherein
Y15 is selected from Leu and Thr;
or a pharmaceutically acceptable salt or solvate thereof.

In specific embodiments, the invention relates to a peptide conjugate having the formula:

H-HGEGTFTSELSKYLEEEAVRLFIEFLKQQYG-
  WLDF-NH$_2$  (Compound 9) (SEQ ID NO: 9)

H-HGEGTFTSELSKYLEEEAVRLFIEF-
  LKQQEAYGWLDF-NH$_2$ (Compound 10) (SEQ ID NO: 10)

H-HGEGTFTSELSKYLEEEAVRLFIEFLK-8Ado-
  QQYGWLDF-NH$_2$  (Compound 11) (SEQ ID NO: 11)

H-HGEGTFTSELSKYLEEEAVRLFIEFLKDYG-
  WLDF-NH$_2$  (Compound 12) (SEQ ID NO: 12)

H-HGEGTFTSELSKYLEEEAVRLFIEFLKAAAYG-
  WLDF-NH$_2$  (Compound 13) (SEQ ID NO: 13)

H-HGEGTFTSELSKYLEEEAVRLFIEFLKGGGYG-
  WLDF-NH$_2$  (Compound 14) (SEQ ID NO: 14)

H-HGEGTFTSELSKYLEEEAVRLFIEFLK-8Aoc-
  YGWLDF-NH$_2$  (Compound 15) (SEQ ID NO: 15)

H-HGEGTFTSELSKYLEEEAVRLFIEFLKNYG-
  WLDF-NH$_2$  (Compound 16) (SEQ ID NO: 16)

H-HGEGTFTSELSKYLEEEAVRLFIEFLKAYG-
  WLDF-NH$_2$  (Compound 17) (SEQ ID NO: 17)

H-HGEGTFTSELSKYLEEEAVRLFIEFLKN-8Ado-
  8Ado-YGWLDF-NH$_2$ (Compound 18) (SEQ ID NO: 18)

H-HGEGTFTSELSKYLEEEAVRLFIEFLKD-8Ado-
  8Ado-YGWLDF-NH$_2$ (Compound 19) (SEQ ID NO: 19)

H-HGEGTFTSELSKYLEEEAVRLFIEFLKNYG-
  WTDF-NH$_2$  (Compound 20) (SEQ ID NO: 20)

H-HGEGTFTSELSKYLEEEAVRLFIEFLKDYG-
  WTDF-NH$_2$  (Compound 21) (SEQ ID NO: 21)

H-HGEGTFTSELSKYLEEEAVRLFIEWLKNYG-
  WLDF-NH$_2$  (Compound 22) (SEQ ID NO: 22)

H-HGEGTFTSELSKYLEEEAVRLFIEWLKDYG-
  WLDF-NH$_2$  (Compound 23) (SEQ ID NO: 23)

or a pharmaceutically acceptable salt or solvate thereof.

In specific embodiments, the peptide conjugates of the invention may be manufactured by standard synthetic methods, by use of recombinant expression systems, or by any other suitable method. Thus, the conjugates may be synthesized in a number of ways, including, e.g., methods comprising:

(a) synthesizing the peptide conjugate by standard solid-phase or liquid-phase methodology, either stepwise or by fragment assembly, and isolating and purifying the final peptide conjugate product;

(b) expressing a nucleic acid construct encoding the peptide conjugate in a host cell and recovering the expression product from the host cell culture; or (c) affecting cell-free in vitro expression of a nucleic acid construct that encodes the peptide conjugate, and recovering the expression product;

or by any combination of the methods of (a), (b) or (c) to obtain fragments of the peptide conjugate, subsequently ligating the fragments to obtain the peptide conjugate, and recovering the peptide conjugate.

Among further embodiments of the invention are methods of treatment of a variety of conditions, diseases or disorders including diabetes (type 1 and type 2) and various diabetes-related conditions, diseases or disorders. These embodiments comprise administration of a peptide conjugate of the invention (in free form or in the form of a pharmaceutically acceptable salt or solvate thereof), as well as pharmaceutical compositions comprising a peptide conjugate or pharmaceutically acceptable salt or solvate thereof of the invention.

In some embodiments, the peptide conjugates of the present invention may be useful as pharmaceutical agents for treatment of insulin resistance, glucose intolerance, pre-diabetes, metabolic syndrome, elevated fasting glucose levels, disease states associated with elevated blood glucose levels, hyperglycemia, type 1 and/or type 2 diabetes, diabetic neuropathy, diabetic retinopathy, diabetic nephropathy, kidney failure, hypertension and/or dyslipidemia (or a combination of these metabolic and cardiovascular risk factors), atherosclerosis, arteriosclerosis, macrovascular disease, microvascular disease, coronary heart disease, peripheral artery disease and stroke. They may also be useful in preventing weight gain, promoting weight loss, reducing excess body weight and/or treating obesity (e.g. by control of appetite, feeding, food intake, calorie intake, and/or energy expenditure), including morbid obesity, as well as associated diseases, disorders and health conditions, including, but not limited to, obesity-linked inflammation, obesity-linked gallbladder disease and obesity-induced sleep apnea. Effects of the peptide conjugates of the invention on these conditions may be mediated in whole or in part via an effect on body weight, or may be independent thereof.

Among further embodiments of the invention are methods of prevention of a variety of conditions, diseases or disorders including diabetes (type 1 and type 2) and various diabetes-related conditions, diseases or disorders. These embodiments comprise administration of a peptide conjugate of the invention (in free form or in the form of a pharmaceutically acceptable salt or solvate thereof), as well as pharmaceutical compositions comprising a peptide conjugate or pharmaceutically acceptable salt or solvate thereof of the invention.

In some embodiments, the peptide conjugates of the present invention may be useful as pharmaceutical agents for prevention of insulin resistance, glucose intolerance, pre-diabetes, metabolic syndrome, elevated fasting glucose levels, disease states associated with elevated blood glucose levels, hyperglycemia, type 1 and/or type 2 diabetes, diabetic neuropathy, diabetic retinopathy, diabetic nephropathy, kidney failure, hypertension and/or dyslipidemia (or a combination of these metabolic and cardiovascular risk factors), atherosclerosis, arteriosclerosis, macrovascular disease, microvascular disease, coronary heart disease, peripheral artery disease and stroke. They may also be useful in preventing weight gain, promoting weight loss, reducing excess body weight and/or treating obesity (e.g. by control of appetite, feeding, food intake, calorie intake, and/or energy expenditure), including morbid obesity, as well as associated diseases, disorders and health conditions, including, but not limited to, obesity-linked inflammation, obesity-linked gallbladder disease and obesity-induced sleep apnea. Effects of the peptide conjugates of the invention on these conditions may be mediated in whole or in part via an effect on body weight, or may be independent thereof.

Further aspects of the invention will become apparent from the disclosure below.

Effect of once daily SC administration of vehicle, liraglutide (100 nmol/kg/day), and Compound 18 (30 and 100 nmol/kg/day) on fasted blood glucose levels after 3 weeks treatment in db/db mice. Data are given as mean values with SEM.

Statistics: Data were compared by 1-way ANOVA followed by Bonferroni's MC test vs. vehicle or vs. liraglutide: ***$p<0.001$ vs. vehicle, ##$p<0.01$ vs. liraglutide.

Figure 2:
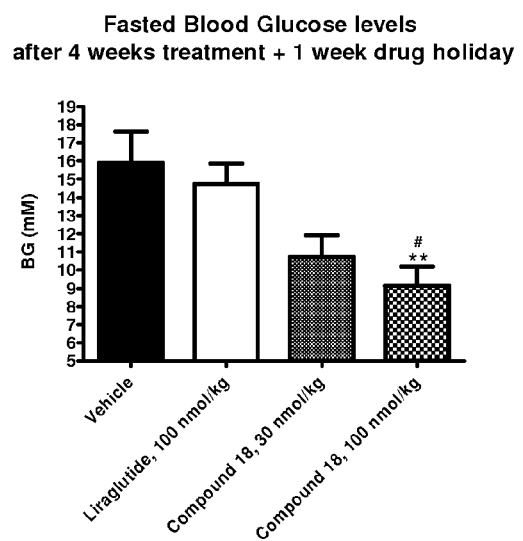

FIG. 2. Fasted Blood Glucose levels after 4 weeks treatment followed by 1 week drug holiday Effect of once daily SC administration of vehicle, liraglutide (100 nmol/kg/day), and Compound 18 (30 and 100 nmol/kg/day) on fasted blood glucose levels after 4 weeks treatment followed by one week drug holiday (vehicle treatment) in db/db mice. Data are given as mean values with SEM.

Statistics: Data were compared by 1-way ANOVA followed by Bonferroni's MC test vs. vehicle or vs. liraglutide: **$p<0.01$ vs. vehicle, #$p<0.05$ vs. liraglutide.

Figure 3:
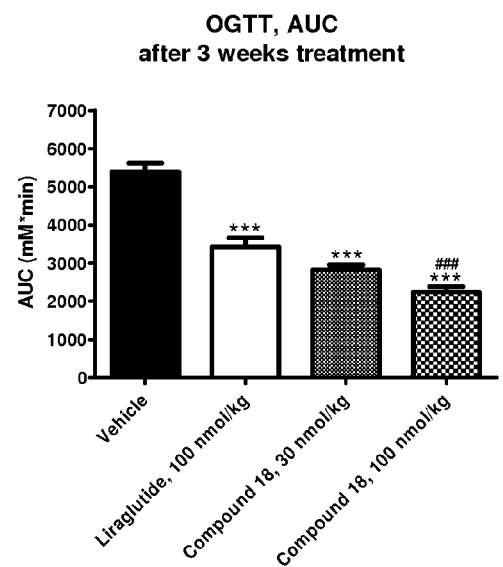

FIG. 3. OGTT, AUC after 3 weeks treatment

Effect of once daily SC administration of vehicle, liraglutide (100 nmol/kg/day), and Compound 18 (30 and 100 nmol/kg/day) on glucose tolerance after 3 weeks treatment in db/db mice. Data are expressed as area under the curve (AUC) with SEM.

Statistics: Data were compared by 1-way ANOVA followed by Bonferroni's MC test vs. vehicle or vs. liraglutide: ***$p<0.001$ vs. vehicle. ###$p<0.001$ vs. liraglutide.

Figure 4:
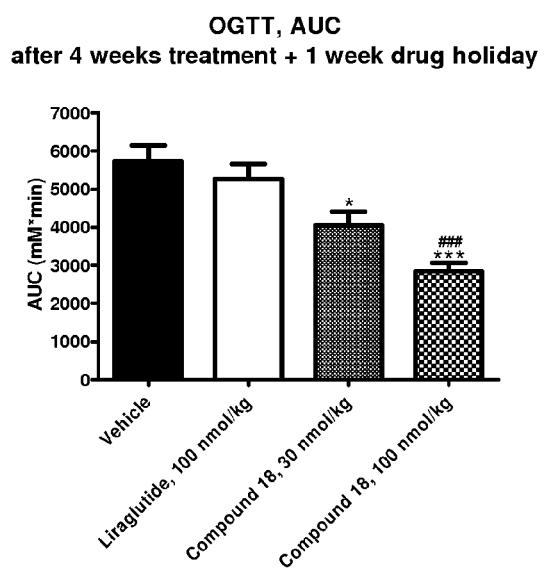

FIG. 4. OGTT, AUC after 4 weeks treatment+1 week drug holiday

Effect of once daily SC administration of vehicle, liraglutide (100 nmol/kg/day), and Compound 18 (30 and 100 nmol/kg/day) on glucose tolerance after 4 weeks treatment followed by one week drug holiday (vehicle treatment) in db/db mice. Data are expressed as area under the curve (AUC) with SEM.

Statistics: Data were compared by 1-way ANOVA followed by Bonferroni's MC test vs. vehicle or vs. liraglutide: *$p<0.05$, ***$p<0.001$ vs. vehicle. ###$p<0.001$ vs. liraglutide.

Figure 5:
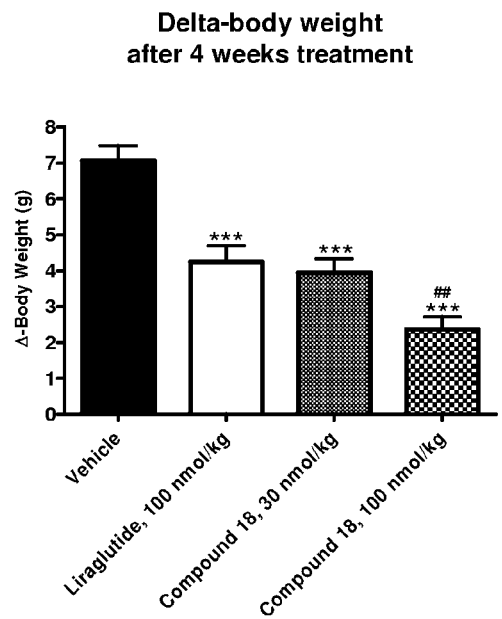

FIG. 5. Delta-body weight after 4 weeks treatment

Effect of once daily SC administration of vehicle, liraglutide (100 nmol/kg/day), and Compound 18 (30 and 100 nmol/kg/day) on delta (termination—start) body weight after 4 weeks treatment in db/db mice. Data are given as mean values with SEM.

Statistics: Data were compared by 1-way ANOVA followed by Bonferroni's MC test vs. vehicle or vs. liraglutide: ***$p<0.001$ vs. vehicle. ##$p<0.01$ vs. liraglutide.

Figure 6:
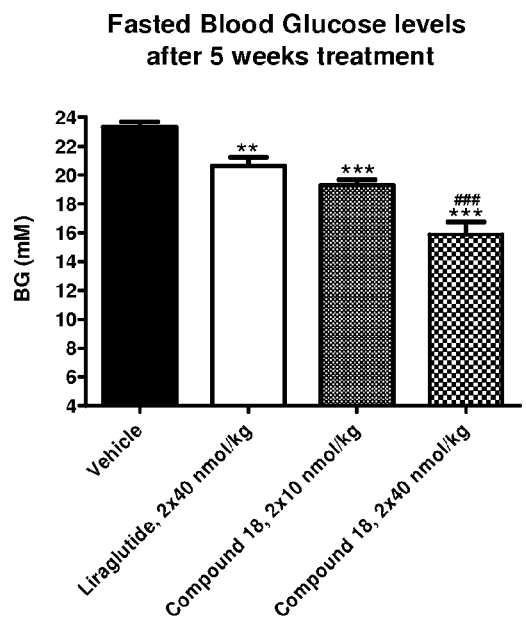

FIG. 6. Fasted Blood Glucose levels after 5 weeks treatment

Effect of twice daily SC administration of vehicle, liraglutide (2×40 nmol/kg/day), and Compound 18 (2×10 and 2×40 nmol/kg/day) on fasted blood glucose levels after 5 weeks treatment in ZDF rats. Data are given as mean values with SEM.

Statistics: Data were compared by 1-way ANOVA followed by Bonferroni's MC test vs. vehicle or vs. liraglutide: $p<0.01$, *$p<0.001$ vs. vehicle, ###$p<0.001$ vs. liraglutide.

FIG. 7. OGTT, AUC after 5 weeks treatment

Effect of once daily SC administration of vehicle, liraglutide (2×40 nmol/kg/day), and Compound 18 (2×10 and 2×40 nmol/kg/day) on glucose tolerance after 5 weeks treatment in db/db mice. Data are expressed as area under the curve (AUC) with SEM.

Statistics: Data were compared by 1-way ANOVA followed by Bonferroni's MC test vs. vehicle or vs. liraglutide: ***$p<0.001$ vs. vehicle. ###$p<0.001$ vs. liraglutide.

FIG. 8. HbA1c levels after 6 weeks treatment

Effect of twice daily SC administration of vehicle, liraglutide (2×40 nmol/kg/day), and Compound 18 (2×10 and 2×40 nmol/kg/day) on HbA1c levels after 6 weeks treatment in ZDF rats. Data are given as mean values with SEM.

Statistics: Data were compared by 1-way ANOVA followed by Bonferroni's MC test vs. vehicle or vs. liraglutide: ***$p<0.001$ vs. vehicle, #$p<0.05$ vs. liraglutide.

DETAILED DESCRIPTION OF THE INVENTION

As indicated above, one aspect of the present invention relates to a peptide conjugate having the formula:

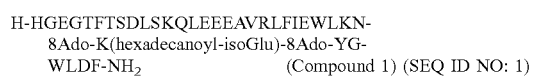
H-HGEGTFTSDLSKQLEEEAVRLFIEWLKN-8Ado-K(hexadecanoyl-isoGlu)-8Ado-YG-WLDF-NH$_2$ (Compound 1) (SEQ ID NO: 1)

H-HGEGTFTSDLSKQLEEEAVRLFIE-K(hexadecanoyl-isoGlu)-LKN-8Ado-8Ado-YGWLDF-NH$_2$ (Compound 2) (SEQ ID NO: 2)

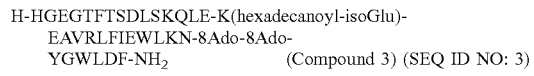
H-HGEGTFTSDLSKQLE-K(hexadecanoyl-isoGlu)-EAVRLFIEWLKN-8Ado-8Ado-YGWLDF-NH$_2$ (Compound 3) (SEQ ID NO: 3)

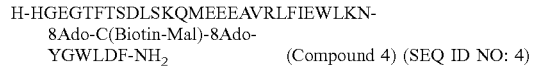
H-HGEGTFTSDLSKQMEEEAVRLFIEWLKN-8Ado-C(Biotin-Mal)-8Ado-YGWLDF-NH$_2$ (Compound 4) (SEQ ID NO: 4)

H-HGEGTFTSDLSKQLEEEAVRLFIE-C(Biotin-Mal)-LKN-8Ado-8Ado-YGWLDF-NH$_2$ (Compound 5) (SEQ ID NO: 5)

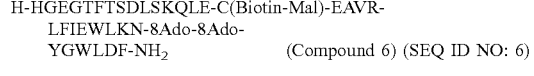
H-HGEGTFTSDLSKQLE-C(Biotin-Mal)-EAVRLFIEWLKN-8Ado-8Ado-YGWLDF-NH$_2$ (Compound 6) (SEQ ID NO: 6)

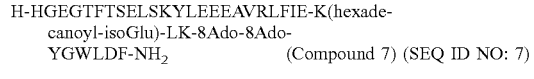
H-HGEGTFTSELSKYLEEEAVRLFIE-K(hexacanoyl-isoGlu)-LK-8Ado-8Ado-YGWLDF-NH$_2$ (Compound 7) (SEQ ID NO: 7)

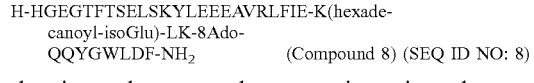
H-HGEGTFTSELSKYLEEEAVRLFIE-K(hexacanoyl-isoGlu)-LK-8Ado-QQYGWLDF-NH$_2$ (Compound 8) (SEQ ID NO: 8)

Further, in another aspect the present invention relates to a peptide conjugate having the formula:

H-HGEGTFTSELSKYLEEEAVRLFIEFLKQQYG-WLDF-NH$_2$ (Compound 9) (SEQ ID NO: 9)

H-HGEGTFTSELSKYLEEEAVRLFIEF-
  LKQQEAYGWLDF-NH₂ (Compound 10) (SEQ ID NO: 10)

H-HGEGTFTSELSKYLEEEAVRLFIEFLK-8Ado-
  QQYGWLDF-NH₂ (Compound 11) (SEQ ID NO: 11)

H-HGEGTFTSELSKYLEEEAVRLFIEFLKDYG-
  WLDF-NH₂ (Compound 12) (SEQ ID NO: 12)

H-HGEGTFTSELSKYLEEEAVRLFIEFLKAAAYG-
  WLDF-NH₂ (Compound 13) (SEQ ID NO: 13)

H-HGEGTFTSELSKYLEEEAVRLFIEFLKGGGYG-
  WLDF-NH₂ (Compound 14) (SEQ ID NO: 14)

H-HGEGTFTSELSKYLEEEAVRLFIEFLK-8Aoc-
  YGWLDF-NH₂ (Compound 15) (SEQ ID NO: 15)

H-HGEGTFTSELSKYLEEEAVRLFIEFLKNYG-
  WLDF-NH₂ (Compound 16) (SEQ ID NO: 16)

H-HGEGTFTSELSKYLEEEAVRLFIEFLKAYG-
  WLDF-NH₂ (Compound 17) (SEQ ID NO: 17)

H-HGEGTFTSELSKYLEEEAVRLFIEFLKN-8Ado-
  8Ado-YGWLDF-NH₂ (Compound 18) (SEQ ID NO: 18)

H-HGEGTFTSELSKYLEEEAVRLFIEFLKD-8Ado-
  8Ado-YGWLDF-NH₂ (Compound 19) (SEQ ID NO: 19)

H-HGEGTFTSELSKYLEEEAVRLFIEFLKNYG-
  WTDF-NH₂ (Compound 20) (SEQ ID NO: 20)

H-HGEGTFTSELSKYLEEEAVRLFIEFLKDYG-
  WTDF-NH₂ (Compound 21) (SEQ ID NO: 21)

H-HGEGTFTSELSKYLEEEAVRLFIEWLKNYG-
  WLDF-NH₂ (Compound 22) (SEQ ID NO: 22)

H-HGEGTFTSELSKYLEEEAVRLFIEWLKDYG-
  WLDF-NH₂ (Compound 23) (SEQ ID NO: 23)

H-HGEGTFTSELSKYLEEEAVRLFIEFLKEAYG-
  WLDF-NH₂ (Compound 24) (SEQ ID NO: 24)

In yet another aspect, the present invention relates to a peptide conjugate having the formula:

H-HGEGTFTSELSKYLEEEAVRLFIEFLKN-K
  (hexadecanoyl-isoGlu)-
  YGWLDF-NH₂ (Compound 25) (SEQ ID NO: 25)

H-HGEGTFTSELSKYLEEEAVRLFIEFLKN-K
  (hexadecanoyl-isoGlu)-
  WLDF-NH₂ (Compound 26) (SEQ ID NO: 26)

H-HGEGTFTSELSKYLE-K(hexadecanoyl-isoGlu)-
  EAVRLFIEFLKNYGWLDF-
  NH₂ (Compound 27) (SEQ ID NO: 27)

H-HGEGTFTSELSKYLE-K(hexadecanoyl-isoGlu)-
  EAVRLFIEFLKNWLDF-
  NH₂ (Compound 28) (SEQ ID NO: 28)

H-HGEGTFTSELSKYLEEEAVRLFIEFLK-K(hexa-
  decanoyl-isoGlu)-YGWLDF-
  NH₂ (Compound 29) (SEQ ID NO: 29)

H-HGEGTFTSELSKYLEEEAVRLFIEFLK-K(hexa-
  decanoyl-isoGlu)-WLDF-
  NH₂ (Compound 30) (SEQ ID NO: 30)

H-HGEGTFTSELSKYLE-K(hexadecanoyl-isoGlu)-
  EAVRLFIEFLKYGWLDF-
  NH₂ (Compound 31) (SEQ ID NO: 31)

H-HGEGTFTSELSKYLE-K(hexadecanoyl-isoGlu)-
  EAVRLFIEFLKWLDF-NH₂ (Compound 32) (SEQ ID NO: 32)

H-HGEGTFTSELSKYLEEEAVRLFIE-K(hexade-
  canoyl-isoGlu)-LK-8Ado-
  YGWLDF-NH₂ (Compound 33) (SEQ ID NO: 33)

H-HGEGTFTSELSKYLEEEAVRLFIE-K(hexade-
  canoyl-isoGlu)-LKQQYGWLDF-
  NH₂ (Compound 34) (SEQ ID NO: 34)

H-HGEGTFTSELSKYLEEEAVRLFIE-K(hexade-
  canoyl-isoGlu)-LK-Orn-Orn-
  YGWLDF-NH₂ (Compound 35) (SEQ ID NO: 35)

H-HGEGTFTSELSKYLEEEAVRLFIE-K(hexade-
  canoyl-isoGlu)-LKNYGWLDF-
  NH₂ (Compound 36) (SEQ ID NO: 36)

H-HGEGTFTSELSKYLEEEAVRLFIE-K(hexade-
  canoyl-isoGlu)-LKDYGWLDF-
  NH₂ (Compound 37) (SEQ ID NO: 37)

In a further aspect, the present invention relates to a peptide conjugate having the formula:

H-HGEGTFTSDLSKQLEEEAVRLFIEC(PEG5K)
  LKN-8Ado-8Ado-YGWLDF-
  NH₂ (Compound 38) (SEQ ID NO: 38)

H-HGEGTFTSELSKYLEEEAVRLFIEC(PEG10K)
  LK-8Ado-8Ado-YGWLDF-
  NH₂ (Compound 39) (SEQ ID NO: 39)

H-HGEGTFTSELSKYLEEEAVRLFIEC(PEG20K)
  LK-8Ado-8Ado-YGWLDF-
  NH₂ (Compound 40) (SEQ ID NO: 40)

H-HGEGTFTSELSKYLEEEAVRLFIEC(PEG40K)
  LK-8Ado-8Ado-YGWLDF-
  NH₂ (Compound 41) (SEQ ID NO: 41)

H-HGEGTFTSDLSKQMEEEAVRLFIEWLKNYG-
  WTDF-OH (Compound 42) (SEQ ID NO: 42)

H-HGEGTFTSELSKYLEEEAVRLFIEFLKN-8Ado-
  8Ado-YGWTDF-NH₂ (Compound 43) (SEQ ID NO: 43)

or a pharmaceutically acceptable salt or solvate thereof.

The abbreviations 8Ado, 8Aoc, Hexadecanoyl, isoGlu, Orn, and Biotin-Mal represent the following non-naturally occurring amino acid moieties, respectively:

8Ado (or Peg3): —NH—CH₂—CH₂—O—CH₂—CH₂—O—CH₂—C(O)— (derived from 8-amino-3,6-dioxaoctanoic acid);

8Aoc: —NH—CH₂—CH₂—CH₂—CH₂—CH₂—CH₂—CH₂—C(O)— (derived from 8-aminooctanoic acid)I;

Hexadecanoyl: CH₃—(CH₂)₁₄—C(O)—;

isoGlu: —NH—CH(COOH)—CH₂—CH₂—C(O)—;

Orn: Ornithine; and

Biotin-Mal: Biotin-maleimide.

With regard to the orientation of the linker moiety in a peptide conjugate of the invention, the linker moiety -8Ado-8Ado-, for example, designates the chemical moiety

—NH—CH₂—CH₂—O—CH₂—CH₂—O—CH₂—C(O)—NH—CH₂—CH₂—O—CH₂—CH₂—O—CH₂—C(O)—, the —NH— . . . moiety at the terminus of the linker moiety in question being covalently attached to the GLP-1 agonist (e.g. exendin-4 derived) moiety of the peptide conjugate in question, and the . . . —C(O)— moiety to the right of the linker moiety in question being attached to the gastrin-derived moiety of the peptide conjugate in question.

In the peptide conjugates of the invention, listed above, it is to be understood that the exendin-4(1-28) peptide sequence moiety is derived from the sequence of the *Heloderma suspectum* exendin-4 sequence or is an analogue thereof.

The term "exendin-4 analogue" in the context of the present invention is defined as a peptide sequence derived from any substitutions, truncations, deletions, additions or conjugations of the native Exendin-4 sequence. This includes but is not limited to the substitutions of the present invention.

Likewise, the [Leu4]gastrin6 moieties in the conjugates are derived synthetically from human gastrin.

Also likewise, the [Leu15]gastrin17 moieties in the conjugates are derived synthetically from human gastrin.

Each one of the above peptide conjugates 1-41 individually, i.e. compound 1 or compound 2 or compound 3 . . . (etc., up to compound 41) or a pharmaceutically acceptable salt or solvate thereof, constitutes a further, individual aspect of the present invention.

In the context of the present invention, unless amino acids are referred to by their full name (e.g. alanine, arginine, etc.), they are designated by their conventional three-letter and/or single-letter abbreviations (e.g. Ala or A for alanine, Arg or R for arginine, etc.).

The term "peptide conjugate" in the context of the present invention refers to a molecule in which a first peptide moiety is attached (i.e. coupled or linked), either directly or via a linking (i.e. bridging or spacing) chemical moiety, by means of covalent chemical bonding to a second peptide moiety.

In peptide conjugates of the invention, exendin-4 or Z ($Z_a$ or $Z_b$) may have at least 75% identity to native *H. suspectum* exendin-4, e.g. at least 80%, 85%, 90%, 95%, 96%, 97%, 98%, 99% or 100% identity.

In the peptide conjugates of the invention, gastrin or Y ($Y_a$ or $Y_b$) may have at least 70% identity to native human gastrin17 and/or gastrin6, e.g., where possible, at least 75%, 80%, 83%, 85%, 90%, 94%, 95%, 96%, 97%, 98%, 99% or 100% identity.

In some embodiments, the polypeptides of the invention may comprise the amino acid sequence set forth in any one of compound No: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and 41 or a functional fragment or variant thereof that is, where possible, at least about 80%, 85%, 90%, 95%, 97%, 98%, 99% or 99.5% identical to one or more of the recited sequences. Amino acid substitutions may be, for example, conservative substitutions.

The term "conservative substitution" as used herein denotes that one or more amino acids is replaced by another, biologically similar residue. Examples include substitution of amino acid residues with similar characteristics, e. g. small amino acids, acidic amino acids, polar amino acids, basic amino acids, hydrophobic amino acids and aromatic amino acids. For example, in a preferred embodiment of the invention Met residues are substituted with norleucine (Nle) which is a bioisostere for Met, but which-as opposed to Met-is not readily oxidised. Another example of a conservative substitution with a residue normally not found in endogenous, mammalian peptides and proteins would be the conservative substitution of Arg or Lys with for example, ornithine, canavanine, aminoethylcysteine or other basic amino acid. For further information concerning phenotypically silent substitutions in peptides and proteins, see, for example, Bowie et. al. *Science* 247, 1306-1310, 1990. Conservative substitutions of amino acids grouped by physicochemical properties. I: neutral, hydrophilic, II: acids and amides, III: basic, IV: hydrophobic, V: aromatic, bulky amino acids.

| I | II | III | IV | V |
|---|---|---|---|---|
| A | N | H | M | F |
| S | D | R | L | Y |
| T | E | K | I | W |
| P | Q |   | V |   |
| G |   |   | C |   |

In some embodiments, the polypeptide of the invention may comprise functional fragments or variants thereof that have at most 20, 15, 10, 9, 8, 7, 6, 5, 4, 3, 2, or 1 amino acid substitutions compared to one or more of the recited sequences. The polypeptide of the invention may further be with or without the signal sequence.

In some embodiments, one or more cysteine of the polypeptides of the invention may be substituted with other residues, such as a serine.

In some embodiments, the polypeptides of the invention share at least 99% amino acid sequence identity to any one of Compound No: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and 41.

The term "pharmaceutically acceptable salt" in the context of the present invention (pharmaceutically acceptable salt of a peptide conjugate of the invention) is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, where $R^1$, $R^2$, $R^3$ and $R^4$ independently will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3$^{rd}$ edition, James Swarbrick (Ed.), Informa Healthcare USA (Inc.), NY, USA, 2007, and in *J. Pharm. Sci.* 66: 2 (1977).

The term "solvate" in the context of the present invention refers to a complex of defined stoichiometry formed between a solute (in casu, a peptide conjugate or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Some embodiments of the invention relate to a peptide conjugate or pharmaceutically acceptable salt thereof according to the invention for use as or the manufacture or preparation of a medicament, or to the use of a peptide conjugate or pharmaceutically acceptable salts thereof in methods of treating or preventing, a variety of diseases or conditions, for example: type 1 diabetes, type 2 diabetes, pre-diabetes, insulin resistance syndrome, impaired glucose tolerance (IGT), disease states associated with elevated blood glucose levels, hyperglycemia, hypertension, atherogenic dyslipidemia, arteriosclerosis (e.g. atherosclerosis), macrovascular disease, coronary heart disease, peripheral artery disease, stroke, microvascular disease, gastric disease, metabolic syndrome, cancer (e.g. colon cancer), inflammatory bowel disease (IBD), irritable bowel syndrome (IBS), diabetic neuropathy, diabetic retinopathy, diabetic nephropathy, and kidney failure.

Further diseases or disorders of possible relevance in this connection include obesity, morbid obesity, obesity-linked inflammation, obesity-linked gall bladder disease and obesity-induced sleep apnea.

In some embodiments, a medicament of the invention is a medicament for use in treating a subject in need thereof.

In further embodiments, the medicament of the invention is a medicament for inducing, in a subject in need thereof, pancreatic islet neogenesis (e.g. for promoting formation of new β-cells in the islets of the pancreas).

In further embodiments, the medicament of the invention is a medicament for inducing, in a subject in need thereof, survival of β-cells in the pancreatic islets (e.g. for preventing loss of β-cells in the pancreatic islets).

In further embodiments, the medicament of the invention is a medicament for inducing, in a subject in need thereof, proliferation of β-cells in the pancreatic islets (e.g. promoting proliferation of existing β-cells in the pancreatic islets).

In further embodiments, the medicament of the invention is a medicament for inducing, in a subject in need thereof, any combination of the above mentioned processes i.e. pancreatic islet neogenesis, survival of β-cells in the pancreatic islets, and/or proliferation of β-cells in the pancreatic islets.

Use of a peptide conjugate or pharmaceutically acceptable salt or solvate thereof according to embodiment claim 39, wherein the medicament is used for improving survival rate of the pancreatic islet β-cell in a subject in need thereof.

In yet other embodiments, the medicament of the invention is a medicament for use in preventing, in a subject in need thereof, β-cell apoptosis and/or necrosis in the pancreatic islets (e.g. for preventing loss of β-cells in the pancreatic islets).

In further embodiments, the medicament of the invention is a medicament for use in reducing, in a subject in need thereof, haemoglobin b1Ac (glycosylated haemoglobin; HbA1c) levels in the blood.

A further aspect of the invention relates to the use of a peptide conjugate of the invention in the manufacture or preparation of a medicament for the treatment, in a subject in need thereof, of one or more of the conditions disclosed herein.

A peptide conjugate of the invention may further be used in:
the manufacture of a medicament for inducing pancreatic islet neogenesis in a subject in need thereof;
the manufacture of a medicament for preventing β-cell apoptosis in the pancreatic islets in a subject in need thereof;
the manufacture of a medicament for use in inducing survival of β-cells in the pancreatic islets in a subject in need thereof;
the manufacture of a medicament for inducing pancreatic β-cells proliferation in a subject in need thereof;
the manufacture of a medicament for reducing haemoglobin b1Ac (glycosylated haemoglobin; HbA1c) levels in the blood of a subject in need thereof;
and/or any combinations thereof.

Among related, additional aspects of the invention are corresponding methods of treatment of conditions, diseases or disorders among those disclosed herein. Thus, one such additional aspect of the invention relates to a method for treatment, in a subject in need thereof, of one or more of the diseases, disorders or conditions disclosed herein, the method comprising administering to the subject a therapeutically effective amount of a peptide conjugate or pharmaceutically acceptable salt or solvate thereof according to the invention.

Further embodiments of the present invention relate to a method for inducing pancreatic islet neogenesis in a subject in need thereof, the method comprising administering to the subject a therapeutically effective amount of a peptide conjugate or pharmaceutically acceptable salt or solvate thereof according to the invention.

Additional embodiments of the invention relate to a method for promoting β-cell survival in the pancreatic islets in a subject in need thereof, the method comprising administering to the subject a therapeutically effective amount of a peptide conjugate or pharmaceutically acceptable salt or solvate thereof according to the invention.

Additional embodiments of the invention relate to a method for reducing or preventing β-cell apoptosis and/or necrosis in the pancreatic islets in a subject in need thereof, the method comprising administering to the subject a therapeutically effective amount of a peptide conjugate or pharmaceutically acceptable salt or solvate thereof according to the invention.

Additional embodiments of the invention relate to a method for inducing β-cell proliferation in the pancreatic islets in a subject in need thereof, the method comprising administering to the subject a therapeutically effective amount of a peptide conjugate or pharmaceutically acceptable salt or solvate thereof according to the invention.

Additional embodiments of the invention relate to a method for inducing any combination of the above mentioned processes, i.e. pancreatic islet neogenesis, survival of β-cells in the pancreatic islets, and/or proliferation of β-cells in the pancreatic islets in a subject in need thereof, the method comprising administering to the subject a therapeutically effective amount of a peptide conjugate or pharmaceutically acceptable salt or solvate thereof according to the invention.

Other embodiments of the invention relate to a method for reducing haemoglobin b1Ac (glycosylated haemoglobin; HbA1c) levels in the blood of a subject in need thereof, the method comprising administering to the subject a therapeutically effective amount of a peptide conjugate or pharmaceutically acceptable salt or solvate thereof according to the invention.

Still further embodiments of the present invention relate to the following:
A method of treatment, in a subject in need thereof, of a disease state associated with elevated blood glucose levels;
A method for lowering blood glucose levels in a subject in need thereof;
A method of stimulating insulin release in a subject in need thereof;
A method for regulating gastric emptying in a subject in need thereof; and
A method for lowering plasma lipid levels in a subject in need thereof.
A method of lowering blood pressure in a subject in need thereof.

A method of lowering body weight in a subject in need thereof.

In each of the latter methods of the invention, the method comprises administering to the subject a therapeutically effective amount of a peptide conjugate or pharmaceutically acceptable salt or solvate thereof according to the invention.

The term "therapeutically effective amount" as employed in the context of the above-described methods of treatment or other therapeutic intervention according to the invention refers to an amount that is sufficient to cure, ameliorate, alleviate or partially arrest the clinical manifestations of the particular disease, disorder or condition that is the object of the treatment or other therapeutic intervention in question e.g. as measured by established clinical endpoints or other biomarkers (established or experimental). A therapeutically relevant amount may be determined empirically by one skilled in the art based on the indication being treated or prevented and the subject to whom the therapeutically relevant amount is being administered. For example, the skilled worker may measure one or more of the clinically relevant indicators of bioactivity described herein, e.g., blood glucose levels, insulin release, and plasma lipid levels. The skilled worker may determine a clinically relevant amount through in vitro or in vivo measurements. Other exemplary measures include weight gain, weight loss, and change in blood pressure.

An amount adequate to accomplish any or all of these effects is defined as a therapeutically effective amount. The administered amount and the method of administration can be tailored to achieve optimal efficacy. An amount effective for a given purpose will depend, inter alia, on the severity of the disease, disorder or condition that is the object of the particular treatment or other therapeutic intervention, on the body weight and general condition of the subject in question, on diet, on possible concurrent medication, and on other factors well known to those skilled in the medical arts. Determination of an appropriate dosage size and dosing regimen most appropriate for administration of a peptide conjugate or pharmaceutically acceptable salt or solvate thereof according to the invention to a human may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are well known to the skilled person.

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g. a human) in need of treatment may thus be a subject already afflicted with the disease or disorder in question. The term "treatment" includes inhibition or reduction of an increase in severity of a pathological state or symptoms (e.g. weight gain or hyperglycemia) relative to the absence of treatment, and is not necessarily meant to imply complete cessation of the relevant disease, disorder or condition.

The terms "preventing" and grammatical variants thereof (e.g., "prevented", "preventing", "prevent") as employed in the present context refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" thus includes slowing the onset of disease relative to the absence of treatment, and is not necessarily meant to imply permanent prevention of the relevant disease, disorder or condition.

The term "agonist" as employed in the context of the invention refers to a substance (ligand) that activates the receptor type in question.

The term "GLP-1 receptor agonist" as employed in the context of the invention (sometimes termed elsewhere "GLP-1 agonist") refers to a substance (ligand) that activates a GLP-1 receptor, such as the human GLP-1 receptor. Substances that activate the human GLP-1 receptor include the native GLP-1 peptide hormones GLP-1(7-37), GLP-1 (7-36)amide, oxyntomodulin, exendin-3, exendin-4, glucagon, gastric inhibitory polypeptide (GIP), and functional peptide analogues and derivatives thereof.

The term "antagonist" as employed in the context of the invention refers to a substance (ligand) that blocks, neutralizes or counteracts the effect of another substance (ligand) that functions as an agonist towards the receptor type in question.

In some embodiments of the invention, a subject in need of the particular treatment or other therapeutic intervention referred to in connection with the various aspects of the invention described above is a mammal. In further embodiments, the mammal is a human.

Additional embodiments of the invention relate to pharmaceutical compositions comprising a peptide conjugate, or a pharmaceutically acceptable salt or solvate thereof, according to the invention, together with a pharmaceutically acceptable carrier, excipient or vehicle.

Synthesis of Peptide Conjugates

The peptide conjugates of the invention may be manufactured by standard synthetic methods, by use of recombinant expression systems, or by any other suitable method. Thus, the conjugates may be synthesized in a number of ways, including, e.g., methods comprising:

(a) synthesizing the peptide conjugate by standard solid-phase or liquid-phase methodology, either stepwise or by fragment assembly, and isolating and purifying the final peptide conjugate product;

(b) expressing a nucleic acid construct that encodes the peptide conjugate in a host cell and recovering the expression product from the host cell culture; or (c) affecting cell-free in vitro expression of a nucleic acid construct encoding the peptide conjugate, nd recovering the expression product;

or by any combination of the methods of (a), (b) or (c) to obtain fragments of the peptide conjugate, subsequently ligating the fragments to obtain the peptide conjugate, and recovering the peptide conjugate.

It may be preferable to synthesize the conjugates of the invention by means of solid-phase or liquid-phase peptide synthesis. In this context, reference may be made to WO 98/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

One or more of the amino acid side chains in the compound of the invention may be further conjugated to a lipophilic substituent. The lipophilic substituent may be covalently bonded to an atom in the amino acid side chain, or alternatively may be conjugated to the amino acid side chain by a spacer. The amino acid may be part of the peptide Z, or a part of peptide L.

Without wishing to be bound by theory, it is thought that the lipophilic substituent binds albumin in the blood stream, thus shielding the compounds of the invention from enzymatic degradation which can enhance the half-life of the compounds. The spacer, when present, may provide spacing between the compound and the lipophilic substituent.

The lipophilic substituent may be attached to the amino acid side chain or to the spacer via an ester, a sulphonyl ester, a thioester, an amide or a sulphonamide. Accordingly it will be understood that in some embodiments the lipophilic substituent includes an acyl group, a sulphonyl group, an N atom, an O atom or an S atom which forms part of the ester, sulphonyl ester, thioester, amide or sulphonamide.

Preferably, an acyl group in the lipophilic substituent forms part of an amide or ester with the amino acid side chain or the spacer.

The lipophilic substituent may include a hydrocarbon chain having 4 to 30 C atoms, for example at least 8 or 12 C atoms, and preferably 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with an acyl group, and accordingly the hydrocarbon chain may be part of an alkanoyl group, for example palmitoyl, caproyl, lauroyl, myristoyl or stearoyl.

Accordingly, the lipophilic substituent may have the formula shown below:

A may be, for example, an acyl group, a sulphonyl group, NH, N-alkyl, an O atom or an S atom, preferably acyl. n is an integer from 3 to 29. In some embodiments, n is least 7 or at least 11. In some embodiments, n is 23 or less. In some embodiments, n is 19 or less.

The hydrocarbon chain may be further substituted. For example, it may be further substituted with up to three substituents selected from $NH_2$, OH and COOH. If the hydrocarbon chain is further substituted, preferably it is further substituted with only one substituent. Alternatively or additionally, the hydrocarbon chain may include a cycloalkane or heterocycloalkane, for example as shown below:

In some embodiments, the cycloalkane or heterocycloalkane is a six-membered ring. In certain preferred embodiments, it is piperidine.

Alternatively, the lipophilic substituent may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As indicated above, the lipophilic substituent may be conjugated to the amino acid side chain by a spacer. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may have the formula:

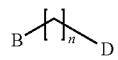

wherein B and D are each independently selected from acyl, sulphonyl, NH, N-alkyl, an O atom or an S atom, preferably from acyl and NH. Preferably, n is an integer from 1 to 10, for example from 1 to 5. The spacer may optionally be further substituted with one or more substituents selected from $C_{1-6}$ alkyl, $C_{1-6}$ alkyl amine, $C_{1-6}$ alkyl hydroxy and $C_{1-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic substituent as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalized side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gln, Asn, α-Glu, γ-Glu, Asp, Ser Thr, Gaba, Aib, bAla, 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from γ-Glu, Gaba, b-Ala and α-Gly.

The lipophilic substituent may be conjugated to any amino acid side chain in the compounds of the invention. Preferably, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. Preferably, the lipophilic substituent is conjugated to Lys or Cys. However, any amino acid shown as Lys in the formulae provided herein may be replaced by Dbu, Dpr or Orn where a lipophilic substituent is added.

An example lipophilic substituent and spacer is shown in the formula below:

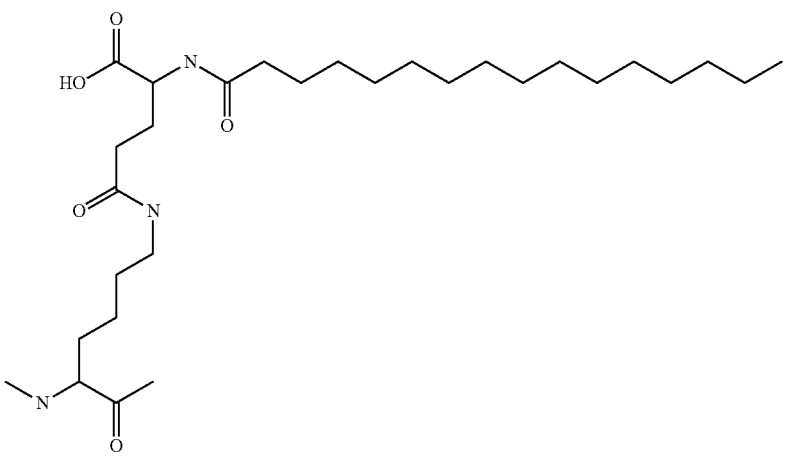 [SMILES: CCCCCCCCCCCCCCCC(=O)NC(CCC(=O)NCCCCC(NC)C(C)=O)C(=O)O]

Here, a Lys from the compound of the present invention (e.g. from X) is covalently attached to γ-Glu (the spacer) by via an amide moiety. Palmitoyl is covalently attached to the γ-Glu spacer via an amide moiety.

Alternatively or additionally, one or more of the amino acid side chains in the compound of the invention may be further conjugated to a biotinylic substituent. The biotinylic substituent may be covalently bonded to an atom in the amino acid side chain, or alternatively may be conjugated to the amino acid side chain by a spacer. The amino acid may be part of the peptide Z, or a part of peptide L.

Without wishing to be bound by theory, it is thought that the biotinylic substituent binds albumin in the blood stream, thus shielding the compounds of the invention from enzymatic degradation which can enhance the half-life of the compounds. The spacer, when present, is used to provide spacing between the compound and the biotinylic substituent.

The biotinylic substituent may be attached to the amino acid side chain or to the spacer via an maleimide ester, a sulphonyl ester, a thioester, an amide or a sulphonamide. Accordingly it will be understood that preferably the biotinylic substituent includes a maleimido group, an acyl group, a sulphonyl group, an N atom, an O atom or an S atom which forms part of the ester, sulphonyl ester, thioester, amide or sulphonamide.

In preferred embodiments the biotin moiety is first coupled to a spacer before the spacer is coupled to the peptide. A number of biotin-spacer conjugates are commercially available with a spacer functionality that will allow coupling to side chains of Lysines or Cysteines. In more preferred embodiments the biotin-spacer conjugate contains a maleimide functionality that can couple selectively to a sulfhydryl group on a Cysteine side chain.

Examples of biotinylic substituents which may be used according to the invention include a)

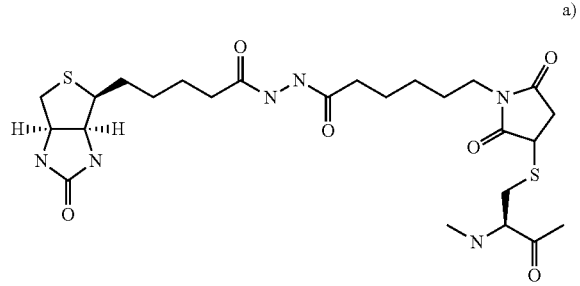 [SMILES: CN[C@@H](CSC1CC(=O)N(CCCCCC(=O)NNC(=O)CCCC[C@@H]2SC[C@@H]3NC(=O)N[C@@H]32)C1=O)C(C)=O]

Biotin is known as Vitamin H or Coenzyme R and is a water-soluble B-complex vitamin (vitamin B7). It has been shown to increase oral uptake of certain drugs.

Alternatively or additionally, one or more amino acid side chains in the compound of the invention may be conjugated to a polymeric moiety, for example, in order to increase solubility and/or half-life in vivo (e.g. in plasma) and/or bioavailability. Such modification is also known to reduce clearance (e.g. renal clearance) of therapeutic proteins and peptides.

The polymeric moiety is preferably water soluble (amphiphilic or hydrophilic), non-toxic, and pharmaceutically inert. Suitable polymeric moieties include polyethylene glycol (PEG), homo- or co-polymers of PEG, a monomethyl-substituted polymer of PEG (mPEG), or polyoxyethylene glycerol (POG). See, for example, *Int. J. Hematology* 68:1 (1998); *Bioconjugate Chem.* 6:150 (1995); and *Crit. Rev. Therap. Drug Carrier Sys.* 9:249 (1992).

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57; Tsukada, et al. (1984), J. Natl. Cancer Inst., vol 73,: 721-729; and Pratesi, et al. (1985), Br. J. Cancer, vol. 52: 841-848).

The polymeric moiety may be straight-chain or branched. It may have a molecular weight of 500-40,000 Da, for example 500-10,000 Da, 1000-5000 Da, 10,000-20,000 Da, or 20,000-40,000 Da.

A compound of the invention may comprise two or more such moieties, in which case the total molecular weight of all such moieties will generally fall within the ranges provided above.

The polymeric moiety may be coupled (by covalent linkage) to an amino, carboxyl or thiol group of an amino acid side chain. Preferred examples are the thiol group of Cys residues and the epsilon amino group of Lys residues, and the carboxyl groups of Asp and Glu residues may also be used.

The skilled worker will be well aware of suitable techniques which can be used to perform the coupling reaction. For example, a PEG moiety carrying a methoxy group can be coupled to a Cys thiol group by a maleimido linkage using reagents commercially available from Nektar Therapeutics AL. See also WO 2008/101017, and the references cited above for details of suitable chemistry.

In some embodiment of the present invention, a maleimide functionalised PEG is conjugated to the side chain sulphydryl group of a Cystein.

Efficacy

A peptide conjugate of the invention has one or more biological activities of exendin-4 and one or more biological activities of gastrin.

The peptide Z ($Z_a$, $Z_b$) in the absence of the gastrin-like component Y ($Y_a$, $Y_b$) and any linker component L ($L_a$, $L_b$), has one or more biological activities of exendin-4. That is to say, a compound $R^1$—Z—$R^2$ would have said one or more biological activities of exendin-4.

The peptide Y ($Y_a$, $Y_b$) in the absence of the exendin-4-like component Z ($Z_a$, $Z_b$) and any linker component L ($L_a$, $L_b$) has one or more biological activities of gastrin. That is to say, a compound $R^1$—Y—$R^2$ would have said one or more biological activities of gastrin.

The biological activity of exendin-4 may be agonist activity at the GLP-1 receptor. The biological activity of gastrin may be agonist activity at the CCK-B receptor.

Preferably the agonist activity is at the human GLP-1 receptor and/or the human CCK-B receptor. "Agonist activity" may involve the ability to induce intracellular cyclic AMP (cAMP) synthesis or pERK phosphorylation on binding to the relevant receptor.

Thus, binding of the relevant compounds to GLP-1 or CCK-B receptors may be used as an indication of agonist activity, but in general it is preferred to use a biological assay which measures intracellular signalling caused by binding of the compound to the relevant receptor. For example, activation of the GLP-1 receptor by a suitable agonist will stimulate cellular cAMP formation. Similarly, activation of the CCK-B receptor by a suitable agonist will stimulate cellular pERK phosphorylation. Thus, production of cAMP or phosphorylation of ERK (pERK) in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The assays may employ the human GLP-1 receptor (NP_002053.3 GI:166795283) and/or the human CCK-B receptor (NM_176875.3 GI:356995851). Where sequences of precursor proteins are referred to, it should of course be understood that assays may make use of the mature protein, lacking the signal sequence.

In a preferred embodiment, the polypeptide of the invention may have an $EC_{50}$ value of below 0.1 nM for GLP1-R.

In some embodiments, the polypeptide of the invention may have an $EC_{50}$ value below 100 nM for CCKB-R In a preferred embodiment, the polypeptide of the invention may have an $EC_{50}$ value of below 50 nM for CCKB-R The $EC_{50}$ values should be measured as described in Example 4.

Therapeutic Uses

Uses of the peptide conjugates of the invention also encompass uses of pharmaceutically acceptable salts or solvates thereof.

The peptide conjugates of the invention may provide an attractive treatment option for metabolic diseases or disorders, including diabetes, in particular type 1 and/or type 2 diabetes, and obesity.

Diabetes comprises a group of metabolic diseases characterized by hyperglycemia resulting from defects in insulin secretion, insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with macro- and microvascular complications that can lead to long-term damage, dysfunction, and—in some cases—ultimately failure of various organs, particularly the eyes (notably in the form of diabetic retinopathy), kidneys (in the form of diabetic nephropathy), nerves (in the form of diabetic neuropathy), heart and blood vessels. Diabetes may be subdivided into three classes, viz. type 1 diabetes, type 2 diabetes and gestational diabetes, on the basis of pathogenetic characteristics.

Type 1 diabetes accounts for 5-10% of all diabetes cases and is caused by auto-immune destruction of insulin-secreting pancreatic β-cells.

Type 2 diabetes accounts for 90-95% of diabetes cases and is a result of a complex set of metabolic disorders. Type 2 diabetes is the consequence of endogenous insulin production and/or whole-body insulin sensitivity becoming insufficient to maintain plasma glucose levels below the diagnostic thresholds.

Gestational diabetes refers to any degree of glucose intolerance identified during pregnancy.

A condition known as pre-diabetes is also recognized. It includes, e.g., elevated fasting glucose levels and impaired glucose tolerance, and refers generally to those states that occur when blood glucose levels are elevated, but are below levels that are established for the clinical diagnosis for diabetes.

A large proportion of subjects with type 2 diabetes and pre-diabetes are at increased risk of morbidity and mortality due to the high prevalence of additional metabolic risk factors, including abdominal obesity (excessive fat tissue around the abdominal internal organs), atherogenic dyslipidemia (blood fat disorders, including high triglyceride levels, low HDL cholesterol levels and/or high LDL cholesterol levels, which foster plaque build-up in artery walls), elevated blood pressure (hypertension), a prothrombotic state (e.g. high Fibrinogen or Plasminogen activator inhibitor-1 levels in the blood), and a proinflammatory state (e.g., elevated C-reactive protein levels in the blood).

Conversely, obesity confers an increased risk of developing, for example, pre-diabetes, type 2 diabetes, certain types of cancer, obstructive sleep apnea and gall-bladder disease.

Dyslipidemia is associated with increased risk of cardiovascular disease. High Density Lipoproteins (HDLs) are of clinical importance since an inverse correlation exists between plasma HDL concentrations and the risk of atherosclerotic disease. The majority of the cholesterol stored in atherosclerotic plaques originates from Low Density Lipoproteins (LDL), and hence elevated concentrations of LDL are closely associated with atherosclerosis. The HDL/LDL ratio is a parameter employed to assess the clinical risk of atherosclerosis and coronary atherosclerosis in particular.

Without being bound by any particular theory, it appears that the peptide conjugates of the invention may unexpectedly combine the physiological effects of GLP-1 receptor agonists with those of gastrin peptides vide supra in a manner such that the observed activity may be significantly greater than that observed when employing a corresponding additive (non-conjugated) combination of the individual peptide components. It is consequently believed that the peptide conjugates of the invention may be of particular benefit in the treatment of pre-diabetes, diabetes (notably type 1 and/or type 2 diabetes) and diabetes-related conditions, diseases or disorders such as those discussed above, including treatment to promote pancreatic islet β-cell formation (islet neogenesis), and thereby insulin production, that will be beneficial with respect to regulation of blood glucose concentrations. Peptide conjugates of the invention may therefore be of value, inter alia, in limiting or arresting disease progression in type 1 and/or type 2 diabetes.

The peptides of the present invention may further be usefull for promoting survival and inhibiting apoptosis of β-cells in the pancreatic islets. Effects of GLP-1 and gastrin includes effects on β-cell proliferation and maturation but also prevention of β-cell apoptosis and/or necrosis and enhanced neogenesis, thus the effects of the peptides of the invention may include such effects and thereof effects on improved insulin and glucose regulation.

The peptide conjugates of the present invention may thus be useful as pharmaceutical agents for treatment of any of the diseases, disorders, or conditions described herein. Exemplary diseases, disorders, or conditions include insulin resistance, glucose intolerance, pre-diabetes, disease states associated with elevated blood glucose levels (e.g., elevated fasting blood glucose levels), type 1 and/or type 2 diabetes, hyperglycemia, gastric disease, metabolic syndrome, hypertension and/or dyslipidemia (or a combination of these metabolic risk factors), atherosclerosis, arteriosclerosis, coronary heart disease, microvascular disease, macrocascular diseases, peripheral artery disease, stroke, cancer (e.g. colon cancer), inflammatory bowel disease (IBD), irritable bowel syndrome (IBS), diabetic neuropathy, diabetic retinopathy, diabetic nephropathy, and kidney failure.

Exemplary effects of treatment include preventing weight gain, promoting weight loss, reducing excess body weight and/or treating obesity (e.g. by control of appetite, feeding, food intake, calorie intake, and/or energy expenditure), including morbid obesity, as well as associated diseases, disorders and health conditions, including, but not limited to, obesity-linked inflammation, obesity-linked gallbladder disease and obesity-induced sleep apnea. Effects of the peptide conjugates of the invention on these conditions may be mediated in whole or in part via an effect on body weight, or may be independent thereof.

Pharmaceutical Compositions

In the following, it will be understood that reference to the inclusion of one or more of a peptide conjugate of the invention in a pharmaceutical composition also encompasses inclusion of a pharmaceutically acceptable salt or solvate of a peptide conjugate of the invention.

The peptide conjugates of the present invention may be formulated as pharmaceutical compositions which are suited for administration with or without storage, and which typically comprise a therapeutically effective amount of at least one peptide conjugate of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration.

Pharmaceutically acceptable carriers or diluents include those used in formulations suitable for e.g. oral, intravitreal, rectal, vaginal, nasal, topical, enteral or parenteral (including subcutaneous (SC), intramuscular (IM), intravenous (IV), intradermal and transdermal) administration or administration by inhalation. The formulations may conveniently be presented in unit dosage form and may be prepared by any of the methods well known in the art of pharmaceutical formulation.

Subcutaneous or transdermal modes of administration may be particularly suitable for the peptide conjugates of the invention.

A further aspect of the invention relates to devices, dosage forms and packages used to deliver the pharmaceutical formulations of the present invention. Thus, at least one peptide conjugate or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

A still further aspect of the invention relates to oral formulations and administration. Formulations for oral administration may rely on the co-administration of adjuvants (e.g., resorcinols and nonionic surfactants such as polyoxyethylene oleyl ether and n-hexadecylpolyethylene ether) to artificially increase the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents, perfuming agents, etc.

Dosages

A typical dosage of a peptide conjugate of the invention as employed in the context of the present invention may be in the range from about 0.0001 to about 100 mg/kg body weight per day, such as from about 0.0005 to about 50 mg/kg body weight per day, such as from about 0.001 to about 10 mg/kg body weight per day, such as from about 0.005 to about 5 mg/kg body weight per day, e.g. from about 0.01 to about 1 mg/kg body weight per day, e.g. from about 0.015 to about 0.1 mg/kg body weight per day administered in one or more doses, such as from one to three doses. As already indicated to some extent above, the exact dosage employed will depend, inter alia, on: the nature and severity of the disease or disorder to be treated; the sex, age, body weight and general condition of the subject to be treated; possible other, concomitant disease or disorder that is undergoing or is to undergo treatment; as well as other factors that will be known to a medical practitioner of skill in the art.

A peptide conjugate of the invention may be administered continuously (e.g., by intravenous administration or another continuous drug administration method), or may be administered to a subject in intervals, typically in regular time intervals, depending on the desired dosage and the pharmaceutical composition selected by the skilled practitioner for the particular subject.

Regular administration dosing intervals include, e.g., once daily, twice daily, once every two, three, four, five or six days, once or twice weekly, once or twice monthly, or a regular and even less frequent dosing interval, depending on the particular dosage formulation, bioavailability, and pharmacokinetic profile of the peptide conjugate.

Such regular peptide conjugate administration regimens of the invention may, in certain circumstances such as, e.g., during chronic long term administration, be advantageously interrupted for an interval of time so that the medicated subject reduces the level of or stops taking the medication, often referred to as taking a "drug holiday." Drug holidays are useful for, e.g., maintaining or regaining sensitivity to a drug especially during long term chronic treatment, or, to reduce unwanted side-effects of long term chronic treatment of the subject with the drug.

The timing of a drug holiday depends on the timing of the regular dosing regimen and the purpose for taking the drug holiday (e.g., to regain drug sensitivity and/or to reduce unwanted side effects of continuous, long term administration). In some embodiments, the drug holiday may be a reduction in the drug (e.g., below the therapeutically effective amount for a certain interval of time). In other embodiments, administration of the drug is stopped for a certain interval of time before administration is started again, at the same or at a different dosing regimen (e.g., at a lower or higher dose and/or frequency of administration).

Thus, the peptide conjugate may be delivered via an administration regime which comprises two or more administration phases separated by respective drug holiday phases.

During each administration phase, the peptide conjugate is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the peptide conjugate to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the peptide conjugate.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of the following drug holiday phase is longer than the dosing interval used in that administration pattern. Where the dosing interval is irregular, the duration of the drug holiday phase may be greater than the mean interval between doses over the course of the administration phase. Alternatively the duration of the drug holiday may be longer than the longest interval between consecutive doses during the administration phase.

The duration of the drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime comprises at least 2 administration phases. Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with the peptide conjugate of the invention, then typically the same combination of drugs or active agents is given in consecutive administration phasesIn certain embodiments, the recipient subject is human.

Combination Therapy

As noted above, it will be understood that reference in the following to a peptide conjugate of the invention also extends to a pharmaceutically acceptable salt or solvate thereof as well as to a composition comprising more than one different peptide conjugate of the invention.

A peptide conjugate of the invention may be administered as part of a combination therapy together with another active agent for the treatment of the disease or disorder in question, e.g. diabetes, obesity, metabolic syndrome, dyslipidemia or hypertension, and in such cases, the two active agents may be given together or separately, e.g. as constituents in the same pharmaceutical composition or formulation, or as separate formulations.

Thus a peptide conjugate of the invention may be used in combination with an anti-diabetic agent of known type, including, but not limited to, metformin, a sulfonylurea, a glinide, a DPP-IV inhibitor, a glitazone, or insulin or an insulin analogue. In a preferred embodiment, the peptide conjugate of the invention is administered in combination with insulin or an analogue thereof, a DPP-IV inhibitor, sulfonylurea or metformin, particularly sulfonylurea or metformin, for achieving adequate glycemic control. In a more preferred embodiment, the peptide conjugate is administered in combination with insulin or an insulin analogue for achieving adequate glycemic control. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™; exendin-4), and Byetta LAR™, lixisenatide (Lyxumia™) and liraglutide (Victoza™)

A peptide conjugate of the invention may also be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human prolslet Peptide (HIP), a melanocortin receptor 4 agonist, liraglutide, Orlistat™ and Sibutramine™ or a melanin concentrating hormone receptor 1 antagonist, CCK, amylin or leptin, and analogues thereof.

A peptide conjugate of the invention may further be used in combination with an anti-hypertension agent of known type, including, but not limited to, an angiotensin-converting enzyme inhibitor, an angiotensin II receptor blocker, a diuretic, a beta-blocker or a calcium channel blocker.

A peptide conjugate of the invention may still further be used in combination with an anti-dyslipidemia agent of known type, including, but not limited to, a statin, a fibrate, a niacin and/or a cholesterol absorption inhibitor.

A peptide conjugate of the invention may also be used in combination with a proton pump inhibitor (i.e. a pharmaceutical agent possessing pharmacological activity as an inhibitor $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™, Pantoprazole™ Rabeprazole™, Zolpidem™, Alpidem™, Saripidem™ or Necopidem™.

A peptide conjugate of the invention may, moreover, be used in combination with an anti-inflammatory agent of known type, including, but not limited to:
steroids and corticosteroids, such as beclomethasone, methylprednisolone, betamethasone, prednisone, dexamethasone, and hydrocortisone;
non-steroidal antiinflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam);
salicylates (e.g. acetylsalicylic acid and sulfasalazine); and pyrazolones (e.g. apazone, bezpiperylon, feprazone, mofebutazone, oxyphenbutazone and phenylbutazone);
COX II inhibitors, such as rofecoxib and celecoxib; preparations of interferon beta (e.g. interferon beta-1a or interferon beta-1b);
and certain other compounds, such as 5-aminosalicylic acid and prodrugs and pharmaceutically acceptable salts thereof.

Metformin has also been demonstrated to have anti-inflammatory properties [see Haffner et al., *Diabetes* 54: 1566-1572 (2005)] and as such may also be useful in the context of the present invention.

The following examples demonstrate certain specific embodiments of the present invention. The following examples were carried out using standard techniques, which are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

Abbreviations employed in the examples include:
NMP: N-methylpyrrolidone
DCM: dichloromethane
DMF: N,N-dimethylformamide
HATU: 2-(7-aza-1H-benzotriazole-1-yl)-1,1,3,3-tetramethyluronium hexafluorophosphate
DIPEA: diisopropylethylamine
EtOH: ethanol
$Et_2O$: diethyl ether
8Ado: 8-amino-3,6-dioxaoctanoyl
8Aoc: 8-aminooctanoyl
TFA: trifluoroacetic acid
MeCN: acetonitrile
HPLC: high performance liquid chromatography
MS: mass spectrometry
IBMX: 3-isobutyl-1-methylxanthine
BSA: bovine serum albumin
cAMP: cyclic adenosine monophosphate
DMEM: Dulbecco's Modified Eagle Medium
FCS: fetal calf serum
HEPES: N-2-hydroxyethylpiperazine-N'-2-ethanesulfonic acid
p-ERK: phosphorylated extracellular regulated kinase
PBS: phosphate-buffered saline
Boc: t-Butoxycarbonyl
NEP: N-Ethylpyrrolidone
Liraglutide: [Arg34, Lys26(Hexadecanoyl-isoGlu)]GLP-1 (7-37)
Synthesis of Compounds
Materials and Methods Unless otherwise specified, reagents and solvents employed in the following were available commercially in standard laboratory reagent or analytical grade, and were used without further purification.
General Procedure for Synthesis of Peptide Conjugates of the Invention Solid phase peptide synthesis was performed on a CEM Liberty Peptide Synthesizer using standard Fmoc chemistry. TentaGel™ S Ram resin (1 g; 0.25 mmol/g) was swelled in NEP (10 ml) prior to use and transferred between tube and reaction vessel using DCM and NEP. Pseudoprolines, which are dipeptides employed to minimize aggregation during peptide synthesis, such as Fmoc-Phe-Thr(ψ-Me,Me-Pro)-OH and Fmoc-Asp-Ser(ψ-Me,Me-Pro)-OH, were used where appropriate, and non-natural amino acids (i.e. Fmoc-8Ado-OH) were employed without any changes to the general procedure.
Coupling:

An Fmoc-amino acid in NEP/DMF/DCM (1:1:1; 0.2 M; 5 ml) was added to the resin in a CEM Discover microwave unit together with HATU/DMF (0.5 M; 2 ml) and DIPEA/NEP (2.0 M; 1 ml). The coupling mixture was heated to 75° C. for 5 min while nitrogen was bubbled through the mixture. The resin was then washed with NEP (4×10 ml).

Deprotection:

Piperidine/NEP (1/4(representing 1 part piperidine to 4 parts NEP); 10 ml) was added to the resin for initial deprotection, and the mixture was microwave-heated (40° C.; 30 sec.). The reaction vessel was drained and a second portion of piperidine/NEP (1/4; 10 ml) was added and heated (75° C.; 3 min) again.

The resin was then washed with NEP (6×10 ml).

Cleavage:

The resin was washed with EtOH (3×10 ml) and Et$_2$O (3×10 ml) and dried to constant weight at room temperature (r.t.). The crude peptide was cleaved from the resin by treatment with TFA/TIS/H$_2$O (90/5/5; 40 ml; 2 h; r.t.). Most of the TFA was removed under reduced pressure, and the crude peptide was precipitated and washed three times with Et$_2$O and dried to constant weight at room temperature.

Purification and Characterisation:

The crude peptide was purified to greater than 90% purity by preparative reverse phase HPLC using a PerSeptive Biosystems VISION Workstation equipped with a suitable column and a fraction collector, and run with a gradient of buffer A (0.1% TFA, aq.) and buffer B (0.1% TFA, 90% MeCN, aq.). Fractions were analysed by analytical HPLC and MS, and relevant fractions were pooled and lyophilised. The final product was characterised by HPLC and MS.

Example 1: Synthesis of Compound 2 [Leu14, Lys25(Hexadecanoyl-isoGlu)]Exendin-4(1-28)-8Ado-8Ado-[Leu4]Gastrin6

[Leu14]Exendin-4(1-28)-8Ado-8Ado-[Leu4]Gastrin6 was synthesized on a CEM Liberty Peptide Synthesizer using TentaGel S Ram resin (1.13 g; 0.24 mmol/g) and Fmoc chemistry as described above. Fmoc-8-amino-3,6-dioxaoctanoic acid (Fmoc-8Ado-OH) was employed as well as Fmoc-Lys(Dde)-OH at the point of attachment for the acylation.

The resin bound protected linear peptide was washed with NMP (3×2 min). The N-terminus of the solid-phase attached peptide was Boc protected using Boc$_2$O (265 mg) and DIPEA (47 µl) in DCM (4 ml) and washed with NMP (5×2 min). The Dde protection group was then cleaved using hydrazine hydrate/NEP (4/96; 2×15 min), and the resin was washed with NMP (5×2 min), DIEA/NMP (1/9; 3×5 min) and NMP (8×2 min). The synthesis was completed on a CEM Liberty Peptide Synthesizer as described above using Fmoc-Glu-OtBu and Hexadecanoic acid.

The peptide was cleaved from the resin as described above, and the purification was performed on a Gemini-NX column (5×25 cm; 10 µm; C18) with a 35 ml/min flow of a mixture of buffer A (0.1% TFA; aq.) and buffer B (0.1% TFA; 90% MeCN; aq.). The product was eluted with a linear gradient from 30% to 65% buffer B over 47 min, and fractions (9 ml) were collected with a fraction collector. Relevant fractions were analysed by analytical HPLC and MS, pooled and lyophilised to give a white powder (39 mg), which was analysed by analytical HPLC as being 81% pure. The mass was 4655.53 Da as determined by MS (Calc. 4655.44 Da).

Example 2: Synthesis of Compound 6 [Cys16(Biotin-Mal),Leu14]Exendin-4(1-28)-8Ado-8Ado-[Leu4]Gastrin6

[Cys16,Leu14]Exendin-4(1-28)-8Ado-8Ado-[Leu4]Gastrin6 was synthesized on a CEM Liberty Peptide Synthesizer using 2 portions of TentaGel S Ram resin (1.12 g; 0.25 mmol/g) and Fmoc chemistry as described above using Fmoc-Phe-Thr(ψ-Me,Me-Pro)-OH and Fmoc-8-amino-3,6-dioxaoctanoic acid (Fmoc-8Ado-OH). The peptide was cleaved from the resin (portion no. 1) as described above.

Purification no. 1: The crude peptide from resin no. 1 was purified on a Gemini-NX column (5×25 cm; 10 µm; C18) with a 35 ml/min flow of a mixture of buffer A (0.1% TFA; aq.) and buffer B (0.1% TFA; 90% MeCN; aq.). The product was eluted with a linear gradient from 30% to 65% buffer B over 47 min, and fractions (9 ml) were collected with a fraction collector. Relevant fractions were analysed by analytical HPLC and MS, pooled and lyophilised to give a white powder (90 mg), which was analysed by analytical HPLC as being 68% pure.

Purification no. 2: The product from purification no. 1 was purified on a Gemini-NX column (10 mm×25 cm; 5 µm; C18) with a 4 ml/min flow of a mixture of buffer A (0.1% TFA; aq.) and buffer B (0.1% TFA; 90% MeCN; aq.). The product was eluted with a linear gradient from 30% to 60% buffer B over 47 min, and fractions (2 ml) were collected with a fraction collector. Relevant fractions were analysed by analytical HPLC and MS, pooled and lyophilised to give a white powder (25 mg), which was analysed by analytical HPLC as being 91% pure.

Purification no. 3: The crude peptide from resin no. 2 was purified on a Gemini column (5×25 cm; 10 µm; C18) with a 35 ml/min flow of a mixture of buffer A (0.1% TFA; aq.) and buffer B (0.1% TFA; 90% MeCN; aq.). The product was eluted with a linear gradient from 30% to 65% buffer B over 47 min, and fractions (9 ml) were collected with a fraction collector. Relevant fractions were analysed by analytical HPLC and MS, pooled and lyophilised to give a white powder (129 mg), which was analysed by analytical HPLC as being 74% pure.

Purification no. 4: The combined products from purifications no. 2 and 3 were purified on a Gemini-NX column (10 mm×25 cm; 5 µm; C18) with a 4 ml/min flow of a mixture of buffer A (0.1% TFA; aq.) and buffer B (0.1% TFA; 90% MeCN; aq.). The product was eluted with a linear gradient from 30% to 55% buffer B over 47 min, and fractions (2 ml) were collected with a fraction collector. Relevant fractions were analysed by analytical HPLC and MS, pooled and lyophilised to give a white powder (32 mg), which was analysed by analytical HPLC as being 73% pure and another white powder (100 mg), which was analysed by analytical HPLC as being 62% pure.

Purification no. 5: The combined products from purification no. 4 was purified on a Gemini-NX column (10 mm×25 cm; 5 µm; C18) with a 4 ml/min flow of a mixture of buffer A (0.1% TFA; aq.) and buffer B (0.1% TFA; 90% MeCN; aq.). The product was eluted with a linear gradient from 30% to 55% buffer B over 47 min, and fractions (2 ml) were collected with a fraction collector. Relevant fractions were analysed by analytical HPLC and MS, pooled and lyophilised to give a white powder (30 mg), which was analysed by analytical HPLC as being 90% pure. The mass was 4320.24 Da as determined by MS (Calc. 4320.12 Da).

Conjugation: The product from purification no. 5 was dissolved in PBS buffer (6 ml; pH 7.4) resulting in a cloudy solution (pH 6.2). Biotin-Maleimide (10.7 mg) was dissolved in DMSO (1.1 ml) and added to the peptide solution. The reaction was monitored by analytical HPLC and purified after 3 hours using a Gemini-NX column (10 mm×25 cm; 5 µm; C18) with a 4 ml/min flow of a mixture of buffer A (0.1% TFA; aq.) and buffer B 60 55% buffer B over 47 min, and fractions (2 ml) were collected with a fraction collector. Relevant fractions were analysed by analytical HPLC and MS, pooled and lyophilised to give a white powder (18 mg), which was analysed by analytical HPLC as being 84% pure. The mass was 4771.35 Da as determined by MS (Calc. 4771.31 Da).

Example 3: Synthesis of Compound 9 [Glu9,Leu14, Phe25,Tyr13]Exendin-4(1-27)-QQ-[Leu4]Gastrin6

The peptide was synthesized on a CEM Liberty Peptide Synthesizer using TentaGel S Ram resin (1.10 g; 0.25 mmol/g) and Fmoc chemistry as described above using Fmoc-Phe-Thr(ψ-Me,Me-Pro)-OH. The peptide was cleaved from the resin as described above. The crude peptide was purified on a Gemini-NX column (5×25 cm; 10 μm; C18) with a 35 ml/min flow of a mixture of buffer A (0.1% TFA; aq.) and buffer B (0.1% TFA; 90% MeCN; aq.). The product was eluted with a linear gradient from 20% to 50% buffer B over 47 min, and fractions (9 ml) were collected with a fraction collector. Relevant fractions were analysed by analytical HPLC and MS, pooled and lyophilised to give a white powder (137 mg), which was analysed by analytical HPLC as being 78% pure. The mass was 4208.11 Da as determined by MS (Calc. 4208.09 Da).

Example 4: Activation ($EC_{50}$) of GLP-1 Receptor and Gastrin CCK-B Receptor In Vitro by Peptide Conjugates of the Invention Materials and Methods
Human GLP-1 Receptor (GLP-1 R) Efficacy Assay:

In vitro effects of peptide conjugates of the invention were assessed by measuring the induction of cAMP following stimulation of the receptor by GLP-1(7-36), exendin-4(1-39) or conjugates of the invention using the FlashPlate™ cAMP kit from Perkin-Elmer. Briefly, HEK293 cells expressing the human GLP-1 R (stable cell line generated through transfection of the cDNA for GLP-1 R and selection of stable clones) were seeded at 40,000 cells/well in 96-well microtiter plates coated with 0.01% poly-L-lysine, and grown for 1 day in culture in 100 μl growth medium [DMEM, 10% FCS, Penicillin (100 IU/ml), Streptomycin (100 μg/ml)]. On the day of analysis, growth medium was removed and the cells were washed once with 200 μl Tyrode buffer [Tyrode's Salts (9.6 g/l), 10 mM HEPES, pH 7.4]. Cells were incubated in 100 μl Tyrode buffer containing increasing concentrations of test compounds, 100 μM IBMX, and 0.1% BSA for 15 min at 37° C. The reaction was stopped by addition of 25 μl 0.5 M HCl and incubated on ice for 60 min. For further methodological details, see WO 2008/152403.

CCK-B Receptor (CCK-B R) Efficacy Assay:

In vitro effects of peptide conjugates of the invention and the control gastrin17 analogue [Leu15]gastrin17 were estimated by measuring p-ERK (using the AlphaScreen™ SureFire p-ERK assay) in HEK293 cells stably expressing the human CCK-B R (high-affinity Gastrin receptor; stable cell line generated through transfection of the cDNA for CCK-B R and selection of stable clone)). The gastrin receptor efficacy assays (AlphaScreen™ SureFire p-ERK assay) were performed as follows: On day 1 the CCK-B R expressing cells were seeded at 20,000 cells/well in 100 μl growth medium [DMEM, 10% FCS, Penicillin (100 IU/ml), Streptomycin (100 μg/ml)] in a 96-well plate coated with poly-D-lysine. The cells were incubated in an incubator (37° C., 5% $CO_2$) for two days. Then the growth medium was changed to 80 μl of serum-free medium [DMEM, Penicillin (100 IU/ml), Streptomycin (100 μg/ml)] per well, and incubation of the cells was continued over night in the incubator.

On the day of analysis, compounds in increasing concentrations were added in 20 μl of serum-free medium containing, and the cells were incubated for 5 min. at room temperature. The stimulation medium was discarded by quickly turning the plate upside down, and 60 μl 1× lysis buffer (from the SureFire assay kit) was added per well. For further details see WO2011/134471.

The peptide conjugates of the invention were tested in the above-described assays (i.e. human GLP-1 R activation efficacy, human CCK-B R activation efficacy).

Exendin-4(1-39) was used as positive control in the human GLP-1 receptor (hGLP-1 R) activation assay, and h[Leu15]Gastrin17 was used as positive control in the human CCK-B receptor (hCCK-B R) activity assay.

The results ($EC_{50}$ values, in nM) are summarized in Table 1 below.

TABLE 1 in vitro activities ($EC_{50}$, nM) of compounds (peptide conjugates) of the invention in activation of hGLP-1 R and hCCK-B R

| Cpd No. | hGLP-1 R $EC_{50}$ (nM) | hCCK-B R $EC_{50}$ (nM) |
|---|---|---|
|  | 0.017 |  |
|  |  | 2.89 |
| 1 | 0.048 | 30 |
| 2 | 0.094 | 7.4 |
| 3 | 0.058 | 38 |
| 4 | 0.14 | 10 |
| 5 | 0.024 | 5.0 |
| 6 | 0.038 | 5.8 |
| 7 | 0.88 | 29 |
| 8 | 0.80 | 21 |
| 9 | 0.093 | 18 |
| 10 | 0.069 | 13 |
| 11 | 0.098 | 59 |
| 12 | 0.13 | 23 |
| 13 | 0.29 | 75 |
| 14 | 0.11 | 28 |
| 15 | 0.17 | 30 |
| 16 | 0.11 | 45 |
| 17 | 0.19 | 85 |
| 18 | 0.062 | 18 |
| 19 | 0.045 | 13 |
| 21 | 0.052 | 94 |
| 22 | 0.085 | 31 |
| 23 | 0.094 | 18 |
| 38 | 0.037 | 61 |
| 40 | 0.37 | 133 |

Results

The results summarized in Table 1 above indicate that the peptide conjugates of the invention are potent agonists of the two receptors in question, and that they exhibit closely similar levels of activity.

Example 5: Pharmacokinetic (PK) of Selected Compounds in Mice

Method

C57BI L/6J mice were given a single subcutaneous dose of 100 nmol/kg of each peptide to be tested. Blood samples were taken after 5 and 30 min and after 1, 2, 4, 6, 16 and 24 hour. At each time point, samples from two mice were taken. The mice were euthanized immediately after blood sampling by cervical dislocation. Plasma samples were analyzed after solid phase extraction (SPE) by liquid chromatography mass spectrometry (LC-MS/MS).

TABLE 2

T½ after s.c. administration of 100 nmol/kg in mice

| Compound | $T_{1/2}$ (h) |
|---|---|
| 7 | 6.2 |
| 12 | 5.0 |
| 18 | 4.1 |
| 19 | 2.4 |
| 22 | 8.2 |
| 23 | 6.7 |

Example 6: Three Weeks In Vivo Db/Db Mouse Study

The db/db mouse model has previously been used to assess the β-cell preserving effects of potential therapeutic candidates [Rolin, B. et al., Am. J. Physiol. Endocrinol. Metab. 283: E745-E752 (2002)]. Several studies have demonstrated a correlation between pancreatic insulin content and β-cell mass [Rolin, B. et al. (loc.cit.); Suarez-Pinzon, W. L. et al., Diabetes 54: 2596-2601 (2005); Suarez-Pinzon W. L. et al., Diabetes 57: 3281-3288 (2008)].

Treatment

Db/db mice were stratified to various treatment groups according to HbA1c levels. Mice were treated once daily with subcutaneous (SC) injections for a total of 21 days. Injection volume was 5 ml/kg. During the study body weights (BW) were recorded daily and used to administer the body weight-corrected doses of peptide.

OGTT

On day 16, an oral glucose tolerance test was performed in the animals. Blood glucose was measured before glucose (at t=0, baseline) and after glucose administration up to 2 hrs.

Termination

At termination the blood glucose levels were measured, and blood samples were analyzed for HbA1c levels.

Measurements

Whole blood glucose concentration (mM) was determined by the immobilized glucose oxidase method (Elite Autoanalyser, Bayer, Denmark). Blood samples were analyzed for HbA1c using the Cobas c111 analyzer (Roche Diagnostics, Mannheim, Germany).

Results

The exendin-gastrin dual agonists Compound 18 and Compound 23 both lowered the fasting blood glucose levels after 16 days treatment. Compound 18 lowered the fasted blood glucose levels to a larger extent than Compound 23. Both compounds lowered the plasma levels of HbA1c after 3 weeks treatment with no significant difference between the compounds (un-paired two-tailed t-test).

Compound 18 and Compound 23 both lowered the area under the glucose concentration curve (AUC) following an oral glucose challenge on day 16 (Table 3), where Compound 18 lowered the glucose concentration to a larger extent than Compound 23.

Finally, both Compound 18 and Compound 23 lowered the body weight gain during the 3 week course of the study (Table 3) where Compound 18 lowered the body weight gain to a larger extent than Compound 23.

TABLE 3

Three weeks in vivo db/db study results

| | Delta-HbA1c (%) | OGTT, AUC (nM*min) | Delta-BW (g) | Fasted BG level (mM) |
|---|---|---|---|---|
| Vehicle | − | − | − | − |
| Compound 18 | +++ | +++ | +++ | +++ |
| Compound 23 | +++ | ++ | ++ | ++ |

Legends to Table 3:
Delta-HbA1c: Effect of SC administration of vehicle, Compound 18 (100 nmol/kg) and Compound 23 (100 nmol/kg) on the delta-HbA1c (%) levels (the level of HbA1c at termination subtracted from the level of HbA1c at initiation of the study) following 21 days treatment of db/db mice. Data are given as mean with SEM (n = 11/group). (−) indicates delta-HbA1c level above 0.5%, (+) indicates delta-HbA1c level between 0.25% and 0.5%, (++) indicates delta-HbA1c level between 0% and 0.25%, (+++) indicates delta-HbA1c level below 0%.
OGTT Area Under the Curve (AUC): Effect of SC administration of vehicle, Compound 18 (100 nmol/kg) and Compound 23 (100 nmol/kg) on glucose tolerance as measured by the Area Under the Curve (AUC) following a glucose load in db/db mice after 16 days of treatment. Data are given as mean with SEM (n = 11/group). (−) indicates OGTT AUC above 3000 mM*min, (+) indicates OGTT AUC between 2000 and 3000 mM*min, (++) indicates OGTT AUC between 1000 and 2000M*min, (+++) indicates OGTT AUC below 1000 mM*min.
Delta-BW: Effect of SC administration of vehicle, Compound 18 (100 nmol/kg) and Compound 23 (100 nmol/kg) on the delta-BW (g) levels (the BW at termination subtracted from the BW at initiation of the study) following 21 days treatment of db/db mice. Data are given as mean with SEM (n = 9-11/group). (−) indicates delta BW above 8 g, (+) indicates delta BW between 6 and 8 g, (++) indicates delta BW between 4 and 6 g, (+++) indicates delta BW below 4 g.
Fasted BG: Effect of SC administration of vehicle, Compound 18 (100 nmol/kg) and Compound 23 (100 nmol/kg) on the fasting blood glucose (mM) levels following 16 days treatment of db/db mice. Data are given as mean with SEM (n = 11/group). (−) indicates fasted BG above 12 mM, (+) indicates fasted BG between 8 and 12 mM, (++) indicates fasted BG between 6 and 8 mM, (+++) indicates fasted BG below 6 mM.

Example 7: In Vivo Db/Db Mouse Study: 4 Weeks Treatment Followed by 2 Weeks Drug Holiday Treatment Db/db mice were stratified to various treatment groups according to HbA1c levels. Mice were treated once daily with subcutaneous (SC) injections for a total of 4 weeks—thereafter they were dosed with vehicle for 2 weeks. Injection volume was 5 ml/kg. During the study body weights (BW) were recorded daily and used to administer the body weight-corrected doses of peptide.

OGTT

After 3 and 5 weeks, an oral glucose tolerance test was performed in the animals. Blood glucose was measured before glucose (at t=0, baseline) and after glucose administration up to 2 hrs.

Measurements

Whole blood glucose concentration (mM) was determined by the immobilized glucose oxidase method (Elite Autoanalyser, Bayer, Denmark).

Results

Figure 1:
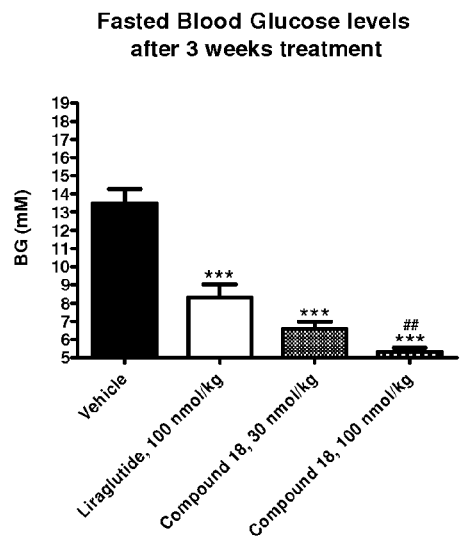
FIG. 1. Fasted Blood Glucose levels after 3 weeks treatment

The exendin-gastrin dual agonist Compound 18 lowered the fasting blood glucose levels after 3 weeks treatment compared to vehicle. Compound 18 lowered the fasted blood glucose levels to a larger extent than liraglutide at equimolar doses, see FIG. 1. After 4 weeks treatment followed by 1 week drug holiday (vehicle dosing), Compound 18 significantly lowered the fasting blood glucose levels compared to vehicle. Compound 18 lowered the fasted blood glucose levels to a larger extent than did liraglutide at equimolar doses, see FIG. 2.

Compound 18 lowered the area under the glucose concentration curve (AUC) following an oral glucose challenge after 3 weeks treatment where Compound 18 lowered the glucose concentration curve (AUC) to a larger extent than did liraglutide, see FIG. 3.

After 4 weeks treatment followed by 1 week drug holiday (vehicle dosing), Compound 18 significantly lowered the area under the glucose concentration curve (AUC) following an oral glucose challenge compared to vehicle, see FIG. 4. Compound 18 lowered the glucose concentration curve (AUC) to a larger extent than did liraglutide at equimolar doses.

Finally, Compound 18 reduced the body weight gain during the 4 week course of the study where Compound 18 lowered the body weight to a larger extent than liraglutide at equimolar doses, see FIG. 5.

Example 8: In Vivo ZDF Rat Study: 6 Weeks Treatment

Treatment

ZDF rats were stratified to various treatment groups according to HbA1c levels. Rats were treated twice daily with subcutaneous (SC) injections for a total of 6 weeks. Injection volume was 5 ml/kg. During the study, body weights (BW) were recorded daily and used to administer the body weight-corrected doses of peptide.

OGTT

After 5 weeks, an oral glucose tolerance test was performed in the animals. Blood glucose was measured before glucose (at t=0, baseline) and after glucose administration up to 2 hrs.

Termination

At termination blood samples were analyzed for HbA1c levels.

Measurements

Whole blood glucose concentration (mM) was determined by the immobilized glucose oxidase method (Elite Autoanalyser, Bayer, Denmark).

Blood samples were analyzed for HbA1c using the Cobas c111 Analyzer (Roche Diagnostics, Mannheim, Germany).

Results

The exendin-gastrin dual agonist Compound 18 lowered the fasting blood glucose levels after 5 weeks treatment compared to vehicle. Compound 18 lowered the fasting blood glucose levels to a larger extent than did liraglutide at equimolar doses, see FIG. 6.

Compound 18 lowered the area under the glucose concentration curve (AUC) following an oral glucose challenge after 5 weeks treatment where Compound 18 lowered the glucose concentration curve (AUC) to a larger extent than did liraglutide, see FIG. 7.

After 6 weeks treatment, Compound 18 significantly lowered the HbA1c levels compared to vehicle. Compound 18 lowered the HbA1c levels to a larger extent than did liraglutide at equimolar doses, see FIG. 8.

The invention claimed is:

1. A peptide conjugate having the formula I $R^1$-$Z_a$-$L_a$-$Y_a$-$R^2$   (I) (SEQ ID No: 45)

wherein $R^1$ is H, $C_{1-4}$ alkyl, acetyl, formyl, benzoyl or trifluoroacetyl; and $R^2$ is OH or $NH_2$;

$Z_a$ is a peptide sequence having the formula Ia

His-Gly-Glu-Gly-Thr-Phe-Thr-Ser-Z9-Leu-Ser-Z12-Z13-Z14-Glu-Z16-Glu-Ala-Val-Z20-Leu-Phe-Ile-Z24-Z25-Leu-Z27-Z28   (Ia) (SEQ ID No: 46)

wherein

Z9 is selected from Asp and Glu;
Z12 is selected from Lys, Arg and Orn;
Z13 is Tyr;
Z14 is Leu;
Z16 is selected from Glu, Arg, Orn, Cys and Lys;
Z20 is selected from Arg, Lys and Orn;
Z24 is selected from Arg, Orn, Lys and Glu;
Z25 is selected from Trp, Lys, Cys and Phe;
Z27 is selected from Lys, Arg and Orn; and
Z28 is selected from Asn and Asp or is absent;
$L_a$ is absent;
$Y_a$ is a peptide sequence having the formula Ic Y12-Y13-Trp-Y15-Asp-Phe   (Ic); (SEQ ID NO: 62)

wherein

Y12 is selected from Tyr and Ala or is absent;
Y13 is selected from Gly and Ala or is absent; and
Y15 is selected from Leu and Thr; and
wherein at least one of Lys, Orn or Cys in formula Ia is further conjugated to a lipophilic and/or a biotinyl substituent and/or pegylated;
or a pharmaceutically acceptable salt thereof.

2. A peptide conjugate according to claim 1 wherein $Z_a$ is a peptide sequence having the formula IIa His-Gly-Glu-Gly-Thr-Phe-Thr-Ser-Z9-Leu-Ser-Lys-Z13-Z14-Glu-Z16-Glu-Ala-Val-Arg-Leu-Phe-Ile-Glu-Z25-Leu-Lys-Z28   (IIa) (SEQ ID NO: 48)

wherein

Z9 is selected from Glu and Asp;
Z13 is Tyr;
Z14 is Leu;
Z16 is selected from Glu, Cys and Lys;
Z25 is selected from Lys, Phe, Cys and Trp; and
Z28 is selected from Asn and Asp or is absent;
$Y_a$ is a peptide sequence having the formula IIc Tyr-Gly-Trp-Y15-Asp-Phe   (IIc) (SEQ ID NO: 49)

wherein

Y15 is selected from Leu and Thr; and
wherein at least one of Lys or Cys in position Z16 or Z25 of formula IIa is further conjugated to a lipophilic and/or a biotinylic substituent and/or pegylated;
or a pharmaceutically acceptable salt thereof.

3. A peptide conjugate or a pharmaceutically acceptable salt thereof according to claim 1 wherein the sequence of the peptide of formula I is selected from:

H-HGEGTFTSELSKYLE-K(hexadecanoyl-isoGlu)-EAVRLFIEFLKNYGWLDF-$NH_2$   (SEQ ID NO: 27);

H-HGEGTFTSELSKYLE-K(hexadecanoyl-isoGlu)-EAVRLFIEFLKNWLDF-$NH_2$   (SEQ ID NO: 28);

H-HGEGTFTSELSKYLE-K(hexadecanoyl-isoGlu)-EAVRLFIEFLKYGWLDF-$NH_2$   (SEQ ID NO: 31);

H-HGEGTFTSELSKYLE-K(hexadecanoyl-isoGlu)-EAVRLFIEFLKWLDF-$NH_2$   (SEQ ID NO: 32);

H-HGEGTFTSELSKYLEEEAVRLFIE-K(hexadecanoyl-isoGlu)-LKNYGWLDF-$NH_2$   (SEQ ID NO: 36); and H-HGEGTFTSELSKYLEEEAVRLFIE-K(hexadecanoyl-isoGlu)-LKDYGWLDF-$NH_2$   (SEQ ID NO: 37).

4. A peptide conjugate having the formula III $R^1$-$Z_b$-$L_b$-$Y_b$-$R^2$   (III) (SEQ ID No: 50)

wherein

R¹ is H, $C_{1-4}$ alkyl, acetyl, formyl, benzoyl or trifluoroacetyl;

R² is OH or $NH_2$;

$Z_b$ is a peptide sequence having the formula IIIa

His-Gly-Glu-Gly-Thr-Phe-Thr-Ser-Glu-Leu-Ser-Lys-
Tyr-Leu-Glu-Glu-Glu-Ala-Val-Arg-Leu-Phe-Ile-
Glu-Z25-Leu-Lys-Z28     (IIIa) (SEQ ID NO: 51)

wherein

Z25 is selected from Phe and Trp; and

Z28 is selected from Asn and Asp or is absent;

$L_b$ is absent;

$Y_b$ is a peptide sequence having the formula IIIc

Y10-Y11-Tyr-Gly-Trp-Y15-Asp-Phe     (IIIc) (SEQ ID NO: 52)

wherein

Y10 is Glu or is absent;

Y11 is Ala or is absent; and

Y15 is selected from Leu and Thr;

or a pharmaceutically acceptable salt thereof;

provided that formula III is not

H-HGEGTFTSELSKYLEEEAVRLFIEFLKYG-
WLDF-$NH_2$     (SEQ ID NO: 54).

5. A peptide conjugate according to claim 4 wherein $Z_b$ is a peptide sequence having the formula IVa His-Gly-Glu-Gly-Thr-Phe-Thr-Ser-Glu-Leu-Ser-Lys-
Tyr-Leu-Glu-Glu-Glu-Ala-Val-Arg-Leu-Phe-Ile-
Glu-Z25-Leu-Lys-Asn     (IVa) (SEQ ID NO: 57)

wherein

Z25 is selected from Phe and Trp; and $Y_b$ is a peptide sequence having the formula IVc Tyr-Gly-Trp-Y15-Asp-Phe     (IVc) (SEQ ID NO: 58)

wherein

Y15 is selected from Leu and Thr;

or a pharmaceutically acceptable salt thereof.

6. A peptide conjugate or a pharmaceutically acceptable salt thereof according to claim 4 wherein the sequence of the peptide of formula III is selected from

H-HGEGTFTSELSKYLEEEAVRLFIEFLKDYG-
WLDF-$NH_2$     (SEQ ID NO: 12);

H-HGEGTFTSELSKYLEEEAVRLFIEFLKNYG-
WLDF-$NH_2$     (SEQ ID NO: 16);

H-HGEGTFTSELSKYLEEEAVRLFIEFLKAYG-
WLDF-$NH_2$     (SEQ ID NO: 17);

H-HGEGTFTSELSKYLEEEAVRLFIEFLKNYG-
WTDF-$NH_2$     (SEQ ID NO: 20);

H-HGEGTFTSELSKYLEEEAVRLFIEFLKDYG-
WTDF-$NH_2$     (SEQ ID NO: 21);

H-HGEGTFTSELSKYLEEEAVRLFIEWLKNYG-
WLDF-$NH_2$     (SEQ ID NO: 22);

H-HGEGTFTSELSKYLEEEAVRLFIEWLKDYG-
WLDF-$NH_2$     (SEQ ID NO: 23); and

H-HGEGTFTSELSKYLEEEAVRLFIEFLKEAYG-
WLDF-$NH_2$     (SEQ ID NO: 24).

7. A method of inducing β-cell neogenesis, islet neogenesis, β-cell survival, and/or β-cell proliferation and/or inhibiting β-cell apoptosis and/or necrosis in the pancreatic islets in a subject in need thereof comprising administering to said subject a peptide conjugate or pharmaceutically acceptable salt thereof according to claim 1.

8. A method of treating or inhibiting the development of a disease or disorder selected from the group consisting of: obesity, type 1 diabetes, type 2 diabetes, pre-diabetes, Insulin resistance syndrome, impaired glucose tolerance (IGT), disease states associated with elevated blood glucose levels, hyperglycemia, hypertension, atherogenic dyslipidemia, arteriosclerosis, macrovascular disease, coronary heart disease, peripheral artery disease, stroke, microvascular disease, gastric disease, metabolic syndrome, cancer, inflammatory bowel disease (IBD), irritable bowel syndrome (IBS), diabetic neuropathy, diabetic retinopathy, diabetic nephropathy, and kidney failure in a subject in need thereof comprising administering to said subject a therapeutically effective amount of a peptide conjugate or pharmaceutically acceptable salt thereof according to claim 1.

9. A pharmaceutical composition comprising a peptide conjugate, or pharmaceutically acceptable salt thereof, according to claim 1, and a pharmaceutically acceptable carrier, excipient or vehicle.

10. A method of inhibiting weight gain, promoting weight loss, improving circulating glucose levels, improving glucose tolerance, improving circulating cholesterol levels, lowering circulating LDL levels, increasing an HDL/LDL ratio, and/or treating a condition caused or characterized by excess body weight in a subject in need thereof comprising administering to said subject a peptide conjugate or pharmaceutically acceptable salt thereof according to claim 1.

11. The method of claim 8, wherein the peptide conjugate or pharmaceutically acceptable salt thereof is administered as part of a combination therapy with a proton pump inhibitor or an agent for treating or inhibiting diabetes, obesity, dyslipidemia, or hypertension.

12. The method of claim 11, wherein the agent for treating or inhibiting diabetes is metformin, a sulfonylurea, a glinide, a DPP-IV inhibitor, a glitazone, insulin or an insulin analogue.

13. The method of claim 11, wherein the agent for treating or inhibiting obesity is a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

14. The method of claim 11, wherein the agent for treating or inhibiting hypertension is an angiotensin-converting enzyme inhibitor, angiotensin II receptor blocker, diuretic, beta-blocker, or calcium channel blocker.

15. The method of claim 11, wherein the agent for treating or inhibiting-dyslipidaemia is a statin, a fibrate, a niacin and/or a cholesterol absorption inhibitor.

16. The method of claim 11, wherein the proton pump inhibitor is an agent of the benzimidazole derivative type or of the imidazopyridine derivative type.

17. A method of synthetically manufacturing a peptide conjugate or pharmaceutically acceptable salt thereof according to claim 1 by solid phase or liquid phase peptide synthesis techniques.

18. A device comprising at least one peptide conjugate or pharmaceutically acceptable salt thereof according to claim 1 for delivering the at least one peptide conjugate or pharmaceutically acceptable salt thereof to a subject.

19. A kit comprising at least one peptide conjugate or pharmaceutically acceptable salt thereof according to claim 1, and packaging or instructions for use.

* * * * *

UNITED STATES PATENT AND TRADEMARK OFFICE
CERTIFICATE OF CORRECTION

PATENT NO. : 9,861,706 B2
APPLICATION NO. : 14/864540
DATED : January 9, 2018
INVENTOR(S) : Jakob Lind Tolborg et al.

It is certified that error appears in the above-identified patent and that said Letters Patent is hereby corrected as shown below:

In the Claims

Column 86, Line 51, in Claim 15, replace "inhibiting-dyslipidaemia" with --inhibiting dyslipidemia--.

Signed and Sealed this
Eleventh Day of September, 2018

Andrei Iancu
*Director of the United States Patent and Trademark Office*

SEQUENCE LISTING

```
<160> NUMBER OF SEQ ID NOS: 63

<210> SEQ ID NO 1
<211> LENGTH: 37
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (29)..(31)
<223> OTHER INFORMATION: Xaa is 8-amino-3,6-dioxaoctanoyl
<220> FEATURE:
<221> NAME/KEY: SITE
<222> LOCATION: (30)..(30)
<223> OTHER INFORMATION: Lys(hexadecanoyl - isoGlu)

<400> SEQUENCE: 1

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Xaa Lys Xaa Tyr
            20                  25                  30

Gly Trp Leu Asp Phe
        35

<210> SEQ ID NO 2
<211> LENGTH: 36
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)
<220> FEATURE:
<221> NAME/KEY: SITE
<222> LOCATION: (29)..(30)
<223> OTHER INFORMATION: Xaa is 8-amino-3,6-dioxaoctanoyl
```

-continued

```
<400> SEQUENCE: 2

His Gly Glu Gly Thr Phe Thr Ser Asp Leu Ser Lys Gln Leu Glu Glu
1               5                   10                  15

Glu Ala Val Arg Leu Phe Ile Glu Lys Leu Lys Asn Xaa Xaa Tyr Gly
            20                  25                  30

Trp Leu Asp Phe
        35

<210> SEQ ID NO 3
<211> LENGTH: 36
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (16)..(16)
<223> OTHER INFORMATION: Lys(hexadecanoyl - isoGlu)
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 3

His Gly Glu Gly Thr Phe Thr Ser Asp Leu Ser Lys Gln Leu Glu Lys
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 4
<211> LENGTH: 37
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (29)..(31)
<223> OTHER INFORMATION: Xaa is 8-amino-3,6-dioxaoctanoyl
<220> FEATURE:
<221> NAME/KEY: SITE
<222> LOCATION: (30)..(30)
<223> OTHER INFORMATION: Cys (Biotin-Mal)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Cys Xaa Tyr
            20                  25                  30

Gly Trp Leu Asp Phe
        35

<210> SEQ ID NO 5
<211> LENGTH: 36
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (25)..(25)
<223> OTHER INFORMATION: Cys (Biotin-Mal)
```

```
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 5

His Gly Glu Gly Thr Phe Thr Ser Asp Leu Ser Lys Gln Leu Glu Glu
1               5                   10                  15

Glu Ala Val Arg Leu Phe Ile Glu Cys Leu Lys Asn Xaa Xaa Tyr Gly
            20                  25                  30

Trp Leu Asp Phe
        35

<210> SEQ ID NO 6
<211> LENGTH: 36
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (16)..(16)
<223> OTHER INFORMATION: Cys (Biotin-Mal)
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 6

His Gly Glu Gly Thr Phe Thr Ser Asp Leu Ser Lys Gln Leu Glu Cys
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 7
<211> LENGTH: 35
<212> TYPE: PRT
<213> ORGANISM: Artificial sequence
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)
<220> FEATURE:
<221> NAME/KEY: SITE
<222> LOCATION: (28)..(29)
<223> OTHER INFORMATION: Xaa is 8-amino-3,6-dioxaoctanoyl

<400> SEQUENCE: 7

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Xaa Xaa Tyr Gly Trp
            20                  25                  30

Leu Asp Phe
        35

<210> SEQ ID NO 8
<211> LENGTH: 36
<212> TYPE: PRT
<213> ORGANISM: Artificial sequence
```

```
<220> FEATURE:
<223> OTHER INFORMATION: Synthetic sequence: Peptide of Formula I of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)
<220> FEATURE:
<221> NAME/KEY: SITE
<222> LOCATION: (28)..(28)
<223> OTHER INFORMATION: Xaa is 8-amino-3,6-dioxaoctanoyl

<400> SEQUENCE: 8

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Xaa Gln Gln Tyr Gly
            20                  25                  30

Trp Leu Asp Phe
        35

<210> SEQ ID NO 9
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 9

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Gln Gln Tyr Gly Trp
            20                  25                  30

Leu Asp Phe
        35

<210> SEQ ID NO 10
<211> LENGTH: 37
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 10

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Gln Gln Glu Ala Tyr
            20                  25                  30

Gly Trp Leu Asp Phe
        35

<210> SEQ ID NO 11
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (28)..(28)
<223> OTHER INFORMATION: Xaa is 8-amino-3,6-dioxaoctanoyl
```

```
<400> SEQUENCE: 11

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Gln Gln Tyr Gly
            20                  25                  30

Trp Leu Asp Phe
        35

<210> SEQ ID NO 12
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 12

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asp Tyr Gly Trp Leu
            20                  25                  30

Asp Phe

<210> SEQ ID NO 13
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 13

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Ala Ala Ala Tyr Gly
            20                  25                  30

Trp Leu Asp Phe
        35

<210> SEQ ID NO 14
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 14

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Gly Gly Gly Tyr Gly
            20                  25                  30

Trp Leu Asp Phe
        35

<210> SEQ ID NO 15
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766
```

```
<220> FEATURE:
<221> NAME/KEY: SITE
<222> LOCATION: (28)..(28)
<223> OTHER INFORMATION: Xaa is 8-aminooctanoyl

<400> SEQUENCE: 15

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Tyr Gly Trp Leu
            20                  25                  30

Asp Phe

<210> SEQ ID NO 16
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 16

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asn Tyr Gly Trp Leu
            20                  25                  30

Asp Phe

<210> SEQ ID NO 17
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 17

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Ala Tyr Gly Trp Leu
            20                  25                  30

Asp Phe

<210> SEQ ID NO 18
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 18

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asn Xaa Xaa Tyr Gly
            20                  25                  30

Trp Leu Asp Phe
        35
```

```
<210> SEQ ID NO 19
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 19

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asp Xaa Xaa Tyr Gly
            20                  25                  30

Trp Leu Asp Phe
        35

<210> SEQ ID NO 20
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 20

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asn Tyr Gly Trp Thr
            20                  25                  30

Asp Phe

<210> SEQ ID NO 21
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 21

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asp Tyr Gly Trp Thr
            20                  25                  30

Asp Phe

<210> SEQ ID NO 22
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 22

His Gly Glu Gly Thr Phe Thr Ser Glu Leu Ser Lys Tyr Leu Glu Glu
1               5                   10                  15

Glu Ala Val Arg Leu Phe Ile Glu Trp Leu Lys Asn Tyr Gly Trp Leu
            20                  25                  30

Asp Phe
```

<210> SEQ ID NO 23
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 23

His Gly Glu Gly Thr Phe Thr Ser Glu Leu Ser Lys Tyr Leu Glu Glu
1               5                   10                  15

Glu Ala Val Arg Leu Phe Ile Glu Trp Leu Lys Asp Tyr Gly Trp Leu
            20                  25                  30

Asp Phe

<210> SEQ ID NO 24
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766

<400> SEQUENCE: 24

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Glu Ala Tyr Gly Trp
            20                  25                  30

Leu Asp Phe
        35

<210> SEQ ID NO 25
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (29)..(29)
<223> OTHER INFORMATION: Lys(hexadecanoyl - isoGlu)

<400> SEQUENCE: 25

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asn Lys Tyr Gly Trp
            20                  25                  30

Leu Asp Phe
        35

<210> SEQ ID NO 26
<211> LENGTH: 33
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (29)..(29)
<223> OTHER INFORMATION: Lys(hexadecanoyl - isoGlu)

```
<400> SEQUENCE: 26

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asn Lys Trp Leu Asp
                20                  25                  30

Phe

<210> SEQ ID NO 27
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (16)..(16)
<223> OTHER INFORMATION: Lys(hexadecanoyl - isoGlu)

<400> SEQUENCE: 27

His Gly Glu Gly Thr Phe Thr Ser Glu Leu Ser Lys Tyr Leu Glu Lys
1               5                   10                  15

Glu Ala Val Arg Leu Phe Ile Glu Phe Leu Lys Asn Tyr Gly Trp Leu
                20                  25                  30

Asp Phe

<210> SEQ ID NO 28
<211> LENGTH: 32
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (16)..(16)
<223> OTHER INFORMATION: Lys(hexadecanoyl - isoGlu)

<400> SEQUENCE: 28

His Gly Glu Gly Thr Phe Thr Ser Glu Leu Ser Lys Tyr Leu Glu Lys
1               5                   10                  15

Glu Ala Val Arg Leu Phe Ile Glu Phe Leu Lys Asn Trp Leu Asp Phe
                20                  25                  30

<210> SEQ ID NO 29
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (28)..(28)
<223> OTHER INFORMATION: Lys(hexadecanoyl - isoGlu)

<400> SEQUENCE: 29

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Lys Tyr Gly Trp Leu
                20                  25                  30

Asp Phe
```

```
<210> SEQ ID NO 30
<211> LENGTH: 32
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (28)..(28)
<223> OTHER INFORMATION: Lys(hexadecanoyl - isoGlu)

<400> SEQUENCE: 30

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Lys Trp Leu Asp Phe
            20                  25                  30

<210> SEQ ID NO 31
<211> LENGTH: 33
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (16)..(16)
<223> OTHER INFORMATION: Lys(hexadecanoyl - isoGlu)

<400> SEQUENCE: 31

His Gly Glu Gly Thr Phe Thr Ser Glu Leu Ser Lys Tyr Leu Glu Lys
1               5                   10                  15

Glu Ala Val Arg Leu Phe Ile Glu Phe Leu Lys Tyr Gly Trp Leu Asp
            20                  25                  30

Phe

<210> SEQ ID NO 32
<211> LENGTH: 31
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (16)..(16)
<223> OTHER INFORMATION: Lys(hexadecanoyl - isoGlu)

<400> SEQUENCE: 32

His Gly Glu Gly Thr Phe Thr Ser Glu Leu Ser Lys Tyr Leu Glu Lys
1               5                   10                  15

Glu Ala Val Arg Leu Phe Ile Glu Phe Leu Lys Trp Leu Asp Phe
            20                  25                  30

<210> SEQ ID NO 33
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)
```

```
<220> FEATURE:
<221> NAME/KEY: SITE
<222> LOCATION: (28)..(28)
<223> OTHER INFORMATION: Xaa is 8-amino-3,6-dioxaoctanoyl

<400> SEQUENCE: 33

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Xaa Tyr Gly Trp Leu
            20                  25                  30

Asp Phe

<210> SEQ ID NO 34
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)

<400> SEQUENCE: 34

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Gln Gln Tyr Gly Trp
            20                  25                  30

Leu Asp Phe
        35

<210> SEQ ID NO 35
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)
<220> FEATURE:
<221> NAME/KEY: MOD_RES
<222> LOCATION: (28)..(29)
<223> OTHER INFORMATION: Orn

<400> SEQUENCE: 35

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Xaa Xaa Tyr Gly Trp
            20                  25                  30

Leu Asp Phe
        35

<210> SEQ ID NO 36
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)
```

```
<400> SEQUENCE: 36

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Asn Tyr Gly Trp Leu
            20                  25                  30

Asp Phe

<210> SEQ ID NO 37
<211> LENGTH: 34
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Lys(hexadecanoyl - isoGlu)

<400> SEQUENCE: 37

His Gly Glu Gly Thr Phe Thr Ser Glu Leu Ser Lys Tyr Leu Glu Glu
1               5                   10                  15

Glu Ala Val Arg Leu Phe Ile Glu Lys Leu Lys Asp Tyr Gly Trp Leu
            20                  25                  30

Asp Phe

<210> SEQ ID NO 38
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Cys (PEG5K)
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 38

His Gly Glu Gly Thr Phe Thr Ser Asp Leu Ser Lys Gln Leu Glu Glu
1               5                   10                  15

Glu Ala Val Arg Leu Phe Ile Glu Cys Leu Lys Asn Xaa Xaa Tyr Gly
            20                  25                  30

Trp Leu Asp Phe
        35

<210> SEQ ID NO 39
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Cys (PEG10K)
<220> FEATURE:
<221> NAME/KEY: SITE
<222> LOCATION: (28)..(29)
<223> OTHER INFORMATION: Xaa is 8-amino-3,6-dioxaoctanoyl
```

```
<400> SEQUENCE: 39

His Gly Glu Gly Thr Phe Thr Ser Glu Leu Ser Lys Tyr Leu Glu Glu
1               5                   10                  15

Glu Ala Val Arg Leu Phe Ile Glu Cys Leu Lys Xaa Xaa Tyr Gly Trp
            20                  25                  30

Leu Asp Phe
        35

<210> SEQ ID NO 40
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Cys (PEG20K)
<220> FEATURE:
<221> NAME/KEY: SITE
<222> LOCATION: (28)..(29)
<223> OTHER INFORMATION: Xaa is 8-amino-3,6-dioxaoctanoyl

<400> SEQUENCE: 40

His Gly Glu Gly Thr Phe Thr Ser Glu Leu Ser Lys Tyr Leu Glu Glu
1               5                   10                  15

Glu Ala Val Arg Leu Phe Ile Glu Cys Leu Lys Xaa Xaa Tyr Gly Trp
            20                  25                  30

Leu Asp Phe
        35

<210> SEQ ID NO 41
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (25)..(25)
<223> OTHER INFORMATION: Cys (PEG40K)
<220> FEATURE:
<221> NAME/KEY: SITE
<222> LOCATION: (28)..(29)
<223> OTHER INFORMATION: Xaa is 8-amino-3,6-dioxaoctanoyl

<400> SEQUENCE: 41

His Gly Glu Gly Thr Phe Thr Ser Glu Leu Ser Lys Tyr Leu Glu Glu
1               5                   10                  15

Glu Ala Val Arg Leu Phe Ile Glu Cys Leu Lys Xaa Xaa Tyr Gly Trp
            20                  25                  30

Leu Asp Phe
        35

<210> SEQ ID NO 42
<211> LENGTH: 35
<212> TYPE: PRT
<213> ORGANISM: Artificial sequence
<220> FEATURE:
<223> OTHER INFORMATION: Synthetic sequence: Peptide of Formula III of
      PCT/EP2012/071766
```

<400> SEQUENCE: 42

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Tyr Gly Trp Thr
                20                  25                  30

Asp Phe His
        35

<210> SEQ ID NO 43
<211> LENGTH: 36
<212> TYPE: PRT
<213> ORGANISM: Artificial sequence
<220> FEATURE:
<223> OTHER INFORMATION: Synthetic sequence: Peptide of Formula III of
      PCT/EP2012/071766
<220> FEATURE:
<221> NAME/KEY: SITE
<222> LOCATION: (29)..(30)
<223> OTHER INFORMATION: Xaa is 8-amino-3,6-dioxaoctanoyl

<400> SEQUENCE: 43

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Asn Xaa Xaa Tyr Gly
                20                  25                  30

Trp Thr Asp Phe
        35

<210> SEQ ID NO 44
<211> LENGTH: 39
<212> TYPE: PRT
<213> ORGANISM: Heloderma suspectum

<400> SEQUENCE: 44

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35

<210> SEQ ID NO 45
<211> LENGTH: 38
<212> TYPE: PRT
<213> ORGANISM: Artificial sequence
<220> FEATURE:
<223> OTHER INFORMATION: Synthetic sequence: Peptide Conjugate. Formula
      I of PCT/EP2012/071766
<220> FEATURE:
<221> NAME/KEY: SITE
<222> LOCATION: (1)..(1)
<223> OTHER INFORMATION: Attached to R1 where R1 is H, C1-4 alkyl,
      acetyl, formyl, benzoyl or trifluoroacetyl
<220> FEATURE:
<221> NAME/KEY: VARIANT
<222> LOCATION: (9)..(9)
<223> OTHER INFORMATION: Xaa is selected from Asp and Glu
<220> FEATURE:
<221> NAME/KEY: VARIANT
<222> LOCATION: (12)..(12)
<223> OTHER INFORMATION: Xaa is selected from Lys, Arg and Orn
<220> FEATURE:
<221> NAME/KEY: VARIANT
<222> LOCATION: (13)..(13)
<223> OTHER INFORMATION: Xaa is selected from Gln and Tyr

```
<220> FEATURE:
<221> NAME/KEY: VARIANT
<222> LOCATION: (14)..(14)
<223> OTHER INFORMATION: Xaa is selected from Met and Leu
<220> FEATURE:
<221> NAME/KEY: VARIANT
<222> LOCATION: (16)..(16)
<223> OTHER INFORMATION: Xaa is selected from Glu, Arg, Orn, Cys and Lys
<220> FEATURE:
<221> NAME/KEY: VARIANT
<222> LOCATION: (20)..(20)
<223> OTHER INFORMATION: Xaa is selected from Arg, Lys and Orn
<220> FEATURE:
<221> NAME/KEY: VARIANT
<222> LOCATION: (24)..(24)
<223> OTHER INFORMATION: Xaa is selected from Arg, Orn, Lys and Glu
<220> FEATURE:
<221> NAME/KEY: VARIANT
<222> LOCATION: (25)..(25)
<223> OTHER INFORMATION: Xaa is selected from Trp, Lys, Cys and Phe
<220> FEATURE:
<221> NAME/KEY: VARIANT
<222> LOCATION: (27)..(27)
<223> OTHER INFORMATION: Xaa is selected from Lys, Arg and Orn
<220> FEATURE:
<221> NAME/KEY: VARIANT
<222> LOCATION: (28)..(28)
<223> OTHER INFORMATION: Xaa is selected from Asn and Asp or is absent
<220> FEATURE:
<221> NAME/KEY: SITE
<222> LOCATION: (29)..(32)
<223> OTHER INFORMATION: Peptide La. Formula Ib
<220> FEATURE:
<221> NAME/KEY: VARIANT
<222> LOCATION: (29)..(32)
<223> OTHER INFORMATION: Xaa is selected from Orn, 8Ado, Cys, Lys and
      Gln or is absent
<220> FEATURE:
<221> NAME/KEY: SITE
<222> LOCATION: (33)..(38)
<223> OTHER INFORMATION: Peptide Ya. Formula Ic
<220> FEATURE:
<221> NAME/KEY: VARIANT
<222> LOCATION: (33)..(33)
<223> OTHER INFORMATION: Xaa is selected from Tyr and Ala or is absent
<220> FEATURE:
<221> NAME/KEY: VARIANT
<222> LOCATION: (34)..(34)
<223> OTHER INFORMATION: Xaa is selected from Gly and Ala or is absent
<220> FEATURE:
<221> NAME/KEY: VARIANT
<222> LOCATION: (35)..(35)
<223> OTHER INFORMATION: Xaa is selected from Trp, 1Nal and Phe
<220> FEATURE:
<221> NAME/KEY: VARIANT
<222> LOCATION: (36)..(36)
<223> OTHER INFORMATION: Xaa is selected from Met, Leu, Nle, Thr and Phe
<220> FEATURE:
<221> NAME/KEY: VARIANT
<222> LOCATION: (38)..(38)
<223> OTHER INFORMATION: Xaa is selected from Phe and 3-(3-pyridyl)-
      alanine
<220> FEATURE:
<221> NAME/KEY: SITE
<222> LOCATION: (38)..(38)
<223> OTHER INFORMATION: Attached to R2 where R2 is OH or NH2

<400> SEQUENCE: 45

His Gly Glu Gly Thr Phe Thr Ser Xaa Leu Ser Xaa Xaa Xaa Glu Xaa
1               5                   10                  15

Glu Ala Val Xaa Leu Phe Ile Xaa Xaa Leu Xaa Xaa Xaa Xaa Xaa Xaa
            20                  25                  30

Xaa Xaa Xaa Xaa Asp Xaa
            35
```

```
<210> SEQ ID NO 46
<211> LENGTH: 28
<212> TYPE: PRT
<213> ORGANISM: Artificial sequence
<220> FEATURE:
<223> OTHER INFORMATION: Synthetic sequence: Peptide Za, having Formula
      Ia of PCT/EP2012/071766
<220> FEATURE:
<221> NAME/KEY: VARIANT
<222> LOCATION: (9)..(9)
<223> OTHER INFORMATION: Xaa is selected from Asp and Glu
<220> FEATURE:
<221> NAME/KEY: VARIANT
<222> LOCATION: (12)..(12)
<223> OTHER INFORMATION: Xaa is selected from Lys, Arg and Orn
<220> FEATURE:
<221> NAME/KEY: VARIANT
<222> LOCATION: (13)..(13)
<223> OTHER INFORMATION: Xaa is selected from Gln and Tyr
<220> FEATURE:
<221> NAME/KEY: VARIANT
<222> LOCATION: (14)..(14)
<223> OTHER INFORMATION: Xaa is selected from Met and Leu
<220> FEATURE:
<221> NAME/KEY: VARIANT
<222> LOCATION: (16)..(16)
<223> OTHER INFORMATION: Xaa is selected from Glu, Arg, Orn, Cys and Lys
<220> FEATURE:
<221> NAME/KEY: VARIANT
<222> LOCATION: (20)..(20)
<223> OTHER INFORMATION: Xaa is selected from Arg, Lys and Orn
<220> FEATURE:
<221> NAME/KEY: VARIANT
<222> LOCATION: (24)..(24)
<223> OTHER INFORMATION: Xaa is selected from Arg, Orn, Lys and Glu
<220> FEATURE:
<221> NAME/KEY: VARIANT
<222> LOCATION: (25)..(25)
<223> OTHER INFORMATION: Xaa is selected from Trp, Lys, Cys and Phe
<220> FEATURE:
<221> NAME/KEY: VARIANT
<222> LOCATION: (27)..(27)
<223> OTHER INFORMATION: Xaa is selected from Lys, Arg and Orn
<220> FEATURE:
<221> NAME/KEY: VARIANT
<222> LOCATION: (28)..(28)
<223> OTHER INFORMATION: Xaa is selected from Asn and Asp or is absent

<400> SEQUENCE: 46

His Gly Glu Gly Thr Phe Thr Ser Xaa Leu Ser Xaa Xaa Xaa Glu Xaa
1               5                   10                  15

Glu Ala Val Xaa Leu Phe Ile Xaa Xaa Leu Xaa Xaa
            20                  25

<210> SEQ ID NO 47
<211> LENGTH: 38
<212> TYPE: PRT
<213> ORGANISM: Artificial sequence
<220> FEATURE:
<223> OTHER INFORMATION: Synthetic sequence: Peptide Conjugate. Formula
      I of PCT/EP2012/071766
<220> FEATURE:
<221> NAME/KEY: SITE
<222> LOCATION: (1)..(1)
<223> OTHER INFORMATION: Attached to R1 where R1 is H, C1-4 alkyl,
      acetyl, formyl, benzoyl or trifluoroacetyl
<220> FEATURE:
<221> NAME/KEY: VARIANT
<222> LOCATION: (9)..(9)
<223> OTHER INFORMATION: Xaa is selected from Glu and Asp
<220> FEATURE:
<221> NAME/KEY: VARIANT
<222> LOCATION: (13)..(13)
<223> OTHER INFORMATION: Xaa is selected from Gln and Tyr
```

```
<220> FEATURE:
<221> NAME/KEY: VARIANT
<222> LOCATION: (14)..(14)
<223> OTHER INFORMATION: Xaa is selected from Met and Leu
<220> FEATURE:
<221> NAME/KEY: VARIANT
<222> LOCATION: (16)..(16)
<223> OTHER INFORMATION: Xaa is selected from Glu, Cys and Lys
<220> FEATURE:
<221> NAME/KEY: VARIANT
<222> LOCATION: (25)..(25)
<223> OTHER INFORMATION: Xaa is selected from Lys, Phe, Cys and Trp
<220> FEATURE:
<221> NAME/KEY: VARIANT
<222> LOCATION: (28)..(28)
<223> OTHER INFORMATION: Xaa is selected from Asn and Asp or is absent
<220> FEATURE:
<221> NAME/KEY: SITE
<222> LOCATION: (29)..(32)
<223> OTHER INFORMATION: Peptide La. Formula Ib
<220> FEATURE:
<221> NAME/KEY: VARIANT
<222> LOCATION: (29)..(32)
<223> OTHER INFORMATION: Xaa is selected from Orn, 8Ado, Cys, Lys and
      Gln or is absent
<220> FEATURE:
<221> NAME/KEY: SITE
<222> LOCATION: (33)..(38)
<223> OTHER INFORMATION: Peptide Ya. Formula IIc, SEQ ID NO: 49
<220> FEATURE:
<221> NAME/KEY: VARIANT
<222> LOCATION: (36)..(36)
<223> OTHER INFORMATION: Xaa is selected from Leu and Thr
<220> FEATURE:
<221> NAME/KEY: SITE
<222> LOCATION: (38)..(38)
<223> OTHER INFORMATION: Attached to R2 where R2 is OH or NH2

<400> SEQUENCE: 47

His Gly Glu Gly Thr Phe Thr Ser Xaa Leu Ser Lys Xaa Xaa Glu Xaa
1               5                   10                  15

Glu Ala Val Arg Leu Phe Ile Glu Xaa Leu Lys Xaa Xaa Xaa Xaa Xaa
            20                  25                  30

Tyr Gly Trp Xaa Asp Phe
        35

<210> SEQ ID NO 48
<211> LENGTH: 28
<212> TYPE: PRT
<213> ORGANISM: Artificial sequence
<220> FEATURE:
<223> OTHER INFORMATION: Synthetic sequence: Peptide Za, having Formula
      IIa of PCT/EP2012/071766
<220> FEATURE:
<221> NAME/KEY: VARIANT
<222> LOCATION: (9)..(9)
<223> OTHER INFORMATION: Xaa is selected from Glu and Asp
<220> FEATURE:
<221> NAME/KEY: VARIANT
<222> LOCATION: (13)..(13)
<223> OTHER INFORMATION: Xaa is selected from Gln and Tyr
<220> FEATURE:
<221> NAME/KEY: VARIANT
<222> LOCATION: (14)..(14)
<223> OTHER INFORMATION: Xaa is selected from Met and Leu
<220> FEATURE:
<221> NAME/KEY: VARIANT
<222> LOCATION: (16)..(16)
<223> OTHER INFORMATION: Xaa is selected from Glu, Cys and Lys
<220> FEATURE:
<221> NAME/KEY: VARIANT
<222> LOCATION: (25)..(25)
<223> OTHER INFORMATION: Xaa is selected from Lys, Phe, Cys and Trp
```

```
<220> FEATURE:
<221> NAME/KEY: VARIANT
<222> LOCATION: (28)..(28)
<223> OTHER INFORMATION: Xaa is selected from Asn and Asp or is absent

<400> SEQUENCE: 48

His Gly Glu Gly Thr Phe Thr Ser Xaa Leu Ser Lys Xaa Xaa Glu Xaa
1               5                   10                  15

Glu Ala Val Arg Leu Phe Ile Glu Xaa Leu Lys Xaa
            20                  25

<210> SEQ ID NO 49
<211> LENGTH: 6
<212> TYPE: PRT
<213> ORGANISM: Artificial sequence
<220> FEATURE:
<223> OTHER INFORMATION: Synthetic sequence: Formula IIc of
      PCT/EP2012/071766
<220> FEATURE:
<221> NAME/KEY: VARIANT
<222> LOCATION: (4)..(4)
<223> OTHER INFORMATION: Xaa is selected from Leu and Thr

<400> SEQUENCE: 49

Tyr Gly Trp Xaa Asp Phe
1               5

<210> SEQ ID NO 50
<211> LENGTH: 40
<212> TYPE: PRT
<213> ORGANISM: Artificial sequence
<220> FEATURE:
<223> OTHER INFORMATION: Synthetic sequence: Peptide Conjugate. Formula
      III of PCT/EP2012/071766
<220> FEATURE:
<221> NAME/KEY: SITE
<222> LOCATION: (1)..(1)
<223> OTHER INFORMATION: Attached to R1 where R1 is H, C1-4 alkyl,
      acetyl, formyl, benzoyl or trifluoroacetyl
<220> FEATURE:
<221> NAME/KEY: VARIANT
<222> LOCATION: (25)..(25)
<223> OTHER INFORMATION: Xaa is selected from Phe and Trp
<220> FEATURE:
<221> NAME/KEY: VARIANT
<222> LOCATION: (28)..(28)
<223> OTHER INFORMATION: Xaa is selected from Asn and Asp or is absent
<220> FEATURE:
<221> NAME/KEY: SITE
<222> LOCATION: (29)..(32)
<223> OTHER INFORMATION: Peptide Lb. Formula IIIb
<220> FEATURE:
<221> NAME/KEY: VARIANT
<222> LOCATION: (29)..(32)
<223> OTHER INFORMATION: Xaa is selected from 8Ado, 8Aoc, Ala, Gly and
      Gln or is absent
<220> FEATURE:
<221> NAME/KEY: SITE
<222> LOCATION: (33)..(40)
<223> OTHER INFORMATION: Peptide Yb. Formula IIIc, SEQ ID NO: 52
<220> FEATURE:
<221> NAME/KEY: VARIANT
<222> LOCATION: (34)..(34)
<223> OTHER INFORMATION: Xaa is Glu or is absent
<220> FEATURE:
<221> NAME/KEY: VARIANT
<222> LOCATION: (35)..(35)
<223> OTHER INFORMATION: Xaa is Ala or is absent
<220> FEATURE:
<221> NAME/KEY: VARIANT
<222> LOCATION: (38)..(38)
<223> OTHER INFORMATION: Xaa is selected from Leu and Thr
```

```
<220> FEATURE:
<221> NAME/KEY: SITE
<222> LOCATION: (40)..(40)
<223> OTHER INFORMATION: Attached to R2 where R2 is OH or NH2

<400> SEQUENCE: 50

His Gly Glu Gly Thr Phe Thr Ser Glu Leu Ser Lys Tyr Leu Glu Glu
1               5                   10                  15

Glu Ala Val Arg Leu Phe Ile Glu Xaa Leu Lys Xaa Xaa Xaa Xaa Xaa
            20                  25                  30

Xaa Xaa Tyr Gly Trp Xaa Asp Phe
        35                  40

<210> SEQ ID NO 51
<211> LENGTH: 28
<212> TYPE: PRT
<213> ORGANISM: Artificial sequence
<220> FEATURE:
<223> OTHER INFORMATION: Synthetic sequence: Peptide Zb, having Formula
      IIIa of PCT/EP2012/071766
<220> FEATURE:
<221> NAME/KEY: VARIANT
<222> LOCATION: (25)..(25)
<223> OTHER INFORMATION: Xaa is selected from Phe and Trp
<220> FEATURE:
<221> NAME/KEY: VARIANT
<222> LOCATION: (28)..(28)
<223> OTHER INFORMATION: Xaa is selected from Asn and Asp or is absent

<400> SEQUENCE: 51

His Gly Glu Gly Thr Phe Thr Ser Glu Leu Ser Lys Tyr Leu Glu Glu
1               5                   10                  15

Glu Ala Val Arg Leu Phe Ile Glu Xaa Leu Lys Xaa
            20                  25

<210> SEQ ID NO 52
<211> LENGTH: 8
<212> TYPE: PRT
<213> ORGANISM: Artificial sequence
<220> FEATURE:
<223> OTHER INFORMATION: Synthetic sequence: Formula IIIc of
      PCT/EP2012/071766
<220> FEATURE:
<221> NAME/KEY: VARIANT
<222> LOCATION: (1)..(1)
<223> OTHER INFORMATION: Xaa is Glu or is absent
<220> FEATURE:
<221> NAME/KEY: VARIANT
<222> LOCATION: (2)..(2)
<223> OTHER INFORMATION: Xaa is Ala or is absent
<220> FEATURE:
<221> NAME/KEY: VARIANT
<222> LOCATION: (6)..(6)
<223> OTHER INFORMATION: Xaa is selected from Leu and Thr

<400> SEQUENCE: 52

Xaa Xaa Tyr Gly Trp Xaa Asp Phe
1               5

<210> SEQ ID NO 53
<211> LENGTH: 35
<212> TYPE: PRT
<213> ORGANISM: Artificial sequence
<220> FEATURE:
<223> OTHER INFORMATION: Synthetic sequence
<220> FEATURE:
<221> NAME/KEY: SITE
<222> LOCATION: (28)..(29)
<223> OTHER INFORMATION: Xaa is 8-amino-3,6-dioxaoctanoyl
```

-continued

```
<400> SEQUENCE: 53

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 54
<211> LENGTH: 33
<212> TYPE: PRT
<213> ORGANISM: Artificial sequence
<220> FEATURE:
<223> OTHER INFORMATION: Synthetic sequence

<400> SEQUENCE: 54

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Tyr Gly Trp Leu Asp
            20                  25                  30

Phe

<210> SEQ ID NO 55
<211> LENGTH: 34
<212> TYPE: PRT
<213> ORGANISM: Artificial sequence
<220> FEATURE:
<223> OTHER INFORMATION: Synthetic sequence
<220> FEATURE:
<221> NAME/KEY: SITE
<222> LOCATION: (28)..(28)
<223> OTHER INFORMATION: Xaa is 8-amino-3,6-dioxaoctanoyl

<400> SEQUENCE: 55

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Tyr Gly Trp Leu
            20                  25                  30

Asp Phe

<210> SEQ ID NO 56
<211> LENGTH: 38
<212> TYPE: PRT
<213> ORGANISM: Artificial sequence
<220> FEATURE:
<223> OTHER INFORMATION: Synthetic sequence: Peptide Conjugate. Formula
      III of PCT/EP2012/071766
<220> FEATURE:
<221> NAME/KEY: SITE
<222> LOCATION: (1)..(1)
<223> OTHER INFORMATION: Attached to R1 where R1 is H, C1-4 alkyl,
      acetyl, formyl, benzoyl or trifluoroacetyl
<220> FEATURE:
<221> NAME/KEY: VARIANT
<222> LOCATION: (25)..(25)
<223> OTHER INFORMATION: Xaa is selected from Phe and Trp
<220> FEATURE:
<221> NAME/KEY: SITE
<222> LOCATION: (29)..(32)
<223> OTHER INFORMATION: Peptide Lb. Formula IIIb
<220> FEATURE:
<221> NAME/KEY: VARIANT
<222> LOCATION: (29)..(32)
<223> OTHER INFORMATION: Xaa is selected from 8Ado, 8Aoc, Ala, Gly and
      Gln or is absent
```

-continued

```
<220> FEATURE:
<221> NAME/KEY: SITE
<222> LOCATION: (33)..(38)
<223> OTHER INFORMATION: Peptide Yb. Formula IVc, SEQ ID NO: 58
<220> FEATURE:
<221> NAME/KEY: VARIANT
<222> LOCATION: (36)..(36)
<223> OTHER INFORMATION: Xaa is selected from Leu and Thr
<220> FEATURE:
<221> NAME/KEY: SITE
<222> LOCATION: (38)..(38)
<223> OTHER INFORMATION: Attached to R2 where R2 is OH or NH2

<400> SEQUENCE: 56

His Gly Glu Gly Thr Phe Thr Ser Glu Leu Ser Lys Tyr Leu Glu Glu
1               5                   10                  15

Glu Ala Val Arg Leu Phe Ile Glu Xaa Leu Lys Asn Xaa Xaa Xaa Xaa
            20                  25                  30

Tyr Gly Trp Xaa Asp Phe
        35

<210> SEQ ID NO 57
<211> LENGTH: 28
<212> TYPE: PRT
<213> ORGANISM: Artificial sequence
<220> FEATURE:
<223> OTHER INFORMATION: Synthetic sequence: Peptide Zb, having Formula
      IVa of PCT/EP2012/071766
<220> FEATURE:
<221> NAME/KEY: VARIANT
<222> LOCATION: (25)..(25)
<223> OTHER INFORMATION: Xaa is selected from Phe and Trp

<400> SEQUENCE: 57

His Gly Glu Gly Thr Phe Thr Ser Glu Leu Ser Lys Tyr Leu Glu Glu
1               5                   10                  15

Glu Ala Val Arg Leu Phe Ile Glu Xaa Leu Lys Asn
            20                  25

<210> SEQ ID NO 58
<211> LENGTH: 6
<212> TYPE: PRT
<213> ORGANISM: Artificial sequence
<220> FEATURE:
<223> OTHER INFORMATION: Synthetic sequence: Formula IVc of
      PCT/EP2012/071766
<220> FEATURE:
<221> NAME/KEY: VARIANT
<222> LOCATION: (4)..(4)
<223> OTHER INFORMATION: Xaa is selected from Leu and Thr

<400> SEQUENCE: 58

Tyr Gly Trp Xaa Asp Phe
1               5

<210> SEQ ID NO 59
<211> LENGTH: 463
<212> TYPE: PRT
<213> ORGANISM: Homo sapiens

<400> SEQUENCE: 59

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45
```

-continued

Ser Leu Thr Glu Asp Pro Pro Ala Thr Asp Leu Phe Cys Asn Arg
 50                  55                  60

Thr Phe Asp Glu Tyr Ala Cys Trp Pro Asp Gly Glu Pro Gly Ser Phe
 65                  70                  75                  80

Val Asn Val Ser Cys Pro Trp Tyr Leu Pro Trp Ala Ser Ser Val Pro
                 85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
            115                 120                 125

Ser Lys Arg Gly Glu Arg Ser Ser Pro Glu Glu Gln Leu Leu Phe Leu
130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
            195                 200                 205

Ala Gln Gln His Gln Trp Asp Gly Leu Leu Ser Tyr Gln Asp Ser Leu
210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Leu Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
            275                 280                 285

Tyr Leu Tyr Glu Asp Glu Gly Cys Trp Thr Arg Asn Ser Asn Met Asn
290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
            355                 360                 365

Phe Val Met Asp Glu His Ala Arg Gly Thr Leu Arg Phe Ile Lys Leu
370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
            435                 440                 445

Ala Gly Ser Ser Met Tyr Thr Ala Thr Cys Gln Ala Ser Cys Ser
450                 455                 460

<210> SEQ ID NO 60
<211> LENGTH: 2206
<212> TYPE: DNA
<213> ORGANISM: Homo sapiens

<400> SEQUENCE: 60

| | | | | | |
|---|---|---|---|---|---|
| agaactcccg | agccagggag | ggggtgcaca | gtcacctggc | gggacagagg | ctggcggagg | 60 |
| gacgggaacc | caggcggggc | gagccgcggg | agagtggagg | gcaggcgcct | gggctggggg | 120 |
| cggggaccag | gcggggcagg | gggcaggag | aggagggcgg | cgggagcctg | agccggaatc | 180 |
| gcagcgtgag | caggtggagc | cgcgttggga | gcccgccggg | tcgagctgag | taaggcggcg | 240 |
| ggctcggcgg | gggccatgga | gctgctaaag | ctgaaccgga | gcgtgcaggg | aaccggaccc | 300 |
| gggccggggg | cttccctgtg | ccgcccgggg | gcgcctctcc | tcaacagcag | cagtgtgggc | 360 |
| aacctcagct | gcgagccccc | tcgcattcgc | ggagccggga | cacgagaatt | ggagctggcc | 420 |
| attagaatca | ctctttacgc | agtgatcttc | ctgatgagcg | ttggaggaaa | tatgctcatc | 480 |
| atcgtggtcc | tgggactgag | ccgccgcctg | aggactgtca | ccaatgcctt | cctcctctca | 540 |
| ctggcagtca | gcgacctcct | gctggctgtg | gcttgcatgc | ccttcaccct | cctgcccaat | 600 |
| ctcatgggca | cattcatctt | tggcaccgtc | atctgcaagg | cggtttccta | cctcatgggg | 660 |
| gtgtctgtga | gtgtgtccac | gctaagcctc | gtggccatcg | cactggagcg | gtacagcgcc | 720 |
| atctgccgac | cactgcaggc | acgagtgtgg | cagacgcgct | cccacgcggc | tcgcgtgatt | 780 |
| gtagccacgt | ggctgctgtc | cggactactc | atggtgccct | accccgtgta | cactgtcgtg | 840 |
| caaccagtgg | ggcctcgtgt | gctgcagtgc | gtgcatcgct | ggcccagtgc | gcgggtccgc | 900 |
| cagacctggt | ccgtactgct | gcttctgctc | ttgttcttca | tcccgggtgt | ggttatggcc | 960 |
| gtggcctacg | ggcttatctc | tcgcgagctc | tacttagggc | ttcgctttga | cggcgacagt | 1020 |
| gacagcgaca | gccaaagcag | ggtccgaaac | caaggcgggc | tgccaggggc | tgttcaccag | 1080 |
| aacgggcgtt | gccggcctga | gactggcgcg | gttggcgaag | acagcgatgg | ctgctacgtg | 1140 |
| caacttccac | gttcccggcc | tgccctggag | ctgacggcgc | tgacggctcc | tgggccggga | 1200 |
| tccggctccc | ggcccaccca | ggccaagctg | ctggctaaga | agcgcgtggt | gcgaatgttg | 1260 |
| ctggtgatcg | ttgtgctttt | ttttctgtgt | tggttgccag | tttatagtgc | caacacgtgg | 1320 |
| cgcgcctttg | atgggcccgg | tgcacaccga | gcactctcgg | gtgctcctat | ctccttcatt | 1380 |
| cacttgctga | gctacgcctc | ggcctgtgtc | aaccccctgg | tctactgctt | catgcaccgt | 1440 |
| cgctttcgcc | aggcctgcct | ggaaacttgc | gctcgctgct | gccccccggcc | tccacgagct | 1500 |
| cgccccaggg | ctcttcccga | tgaggaccct | cccactccct | ccattgcttc | gctgtccagg | 1560 |
| cttagctaca | ccaccatcag | cacactgggc | cctggctgag | gagtagaggg | gccgtggggg | 1620 |
| ttgaggcagg | gcaaatgaca | tgcactgacc | cttccagaca | tacgaaacac | aaaccacaac | 1680 |
| tgacacagga | aaccaacacc | caaagcatgg | actaacccca | cgcacagga | aaaggtagct | 1740 |
| tacctgacac | aagaggaata | agaatggagc | agtacatggg | aaaggaggca | tgcctctgat | 1800 |
| atgggactga | gcctggccca | tagaaacatg | acactgacct | tggagagaca | cagcgtccct | 1860 |
| agcagtgaac | tatttctaca | cagtgggaac | tctgacaagg | gctgacctgc | ctctcacaca | 1920 |
| catagattaa | tggcactgat | tgttttagag | actatggagc | ctggcacagg | actgactctg | 1980 |
| ggatgctcct | agtttgacct | cacagtgacc | cttcccaatc | agcactgaaa | ataccatcag | 2040 |
| gcctaatctc | atacctctga | ccaacaggct | gttctgcact | gaaaaggttc | ttcatccctt | 2100 |

```
tccagttaag gaccgtggcc ctgccctctc cttccttacc caaactgttc aagaaataat    2160
aaattgtttg gcttcctcct gaaaaaaaaa aaaaaaaaa aaaaaa                    2206
```

<210> SEQ ID NO 61
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is Orn, 8-amino-3,6-dioxaoctanoic acid
      derivative, Cys, Lys, Gln, or absent
<220> FEATURE:
<221> NAME/KEY: MISC_FEATURE
<222> LOCATION: (2)..(2)
<223> OTHER INFORMATION: Xaa is Orn, 8-amino-3,6-dioxaoctanoic acid
      derivative, Cys, Lys, Gln, or absent
<220> FEATURE:
<221> NAME/KEY: MISC_FEATURE
<222> LOCATION: (3)..(3)
<223> OTHER INFORMATION: Xaa is Orn, 8-amino-3,6-dioxaoctanoic acid
      derivative, Cys, Lys, Gln, or absent
<220> FEATURE:
<221> NAME/KEY: MISC_FEATURE
<222> LOCATION: (4)..(4)
<223> OTHER INFORMATION: Xaa is Orn, 8-amino-3,6-dioxaoctanoic acid
      derivative, Cys, Lys, Gln, or absent

<400> SEQUENCE: 61

Xaa Xaa Xaa Xaa
1

<210> SEQ ID NO 62
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is Tyr, Ala, or absent
<220> FEATURE:
<221> NAME/KEY: MISC_FEATURE
<222> LOCATION: (2)..(2)
<223> OTHER INFORMATION: Xaa is Gly, Ala, or absent
<220> FEATURE:
<221> NAME/KEY: MISC_FEATURE
<222> LOCATION: (3)..(3)
<223> OTHER INFORMATION: Xaa is Trp, L-1-Naphthylalanine, or Phe
<220> FEATURE:
<221> NAME/KEY: MISC_FEATURE
<222> LOCATION: (4)..(4)
<223> OTHER INFORMATION: Xaa is Met, Leu, Nle, Thr, or Phe
<220> FEATURE:
<221> NAME/KEY: MISC_FEATURE
<222> LOCATION: (6)..(6)
<223> OTHER INFORMATION: Xaa is Phe or 3-(3-pyridyl)-alanine

<400> SEQUENCE: 62

Xaa Xaa Xaa Xaa Asp Xaa
1               5

<210> SEQ ID NO 63
<211> LENGTH: 4
<212> TYPE: PRT
<213> ORGANISM: Artificial Sequence
<220> FEATURE:
<223> OTHER INFORMATION: synthetic construct

```
<220> FEATURE:
<221> NAME/KEY: MISC_FEATURE
<222> LOCATION: (1)..(1)
<223> OTHER INFORMATION: Xaa is 8-amino-3,6-dioxaoctanoic acid
      derivative, 8-aminooctanoic acid derivative, Ala, Gly, Gln, or
      absent
<220> FEATURE:
<221> NAME/KEY: MISC_FEATURE
<222> LOCATION: (2)..(2)
<223> OTHER INFORMATION: Xaa is 8-amino-3,6-dioxaoctanoic acid
      derivative, 8-aminooctanoic acid derivative, Ala, Gly, Gln, or
      absent
<220> FEATURE:
<221> NAME/KEY: MISC_FEATURE
<222> LOCATION: (3)..(3)
<223> OTHER INFORMATION: Xaa is 8-amino-3,6-dioxaoctanoic acid
      derivative, 8-aminooctanoic acid derivative, Ala, Gly, Gln, or
      absent
<220> FEATURE:
<221> NAME/KEY: MISC_FEATURE
<222> LOCATION: (4)..(4)
<223> OTHER INFORMATION: Xaa is 8-amino-3,6-dioxaoctanoic acid
      derivative, 8-aminooctanoic acid derivative, Ala, Gly, Gln, or
      absent

<400> SEQUENCE: 63

Xaa Xaa Xaa Xaa
1
```